United States Patent
Mai et al.

(10) Patent No.: US 9,758,830 B2
(45) Date of Patent: Sep. 12, 2017

(54) METHODS FOR EVALUATING ALZHEIMER'S DISEASE AND DISEASE SEVERITY

(71) Applicant: 3D Signatures Inc., Winnipeg (CA)

(72) Inventors: Sabine Mai, Winnipeg (CA); Angeles Garcia, Kingston (CA)

(73) Assignee: 3D SIGNATURES INC., Winnipeg (CA)

(*) Notice: Subject to any disclaimer, the term of this patent is extended or adjusted under 35 U.S.C. 154(b) by 0 days.

(21) Appl. No.: 14/491,996

(22) Filed: Sep. 20, 2014

(65) Prior Publication Data

US 2015/0167058 A1  Jun. 18, 2015

Related U.S. Application Data

(60) Provisional application No. 61/880,274, filed on Sep. 20, 2013.

(51) Int. Cl.
C12Q 1/68 (2006.01)

(52) U.S. Cl.
CPC ......... *C12Q 1/6883* (2013.01); *C12Q 1/6841* (2013.01)

(58) Field of Classification Search
None
See application file for complete search history.

(56) References Cited

U.S. PATENT DOCUMENTS

| | | | |
|---|---|---|---|
| 6,506,563 B1 | 1/2003 | Ward et al. | |
| 7,801,682 B2* | 9/2010 | Mai | C12Q 1/68 382/133 |
| 8,084,203 B2 | 12/2011 | Flores Hernandez et al. | |
| 8,849,579 B2 | 9/2014 | Mai et al. | |
| 2002/0012472 A1 | 1/2002 | Waterfall et al. | |
| 2013/0178435 A1* | 7/2013 | Mai | C12Q 1/6886 514/32 |
| 2015/0004603 A1* | 1/2015 | Mai | C12Q 1/6883 435/6.11 |

FOREIGN PATENT DOCUMENTS

| | | |
|---|---|---|
| WO | 99/66075 A2 | 12/1999 |
| WO | 2010/118419 A2 | 10/2010 |

OTHER PUBLICATIONS

Figueroa et al Cancer Research. 2000. 60: 2770-2774.*
Lansdorp et al. Human Molec Genet. 1996. 5(5): 685-691.*
Garcia, Angeles et al. Three-Dimensional Telomere Analysis in Alzheimer's Disease (AD). Alzheimer's and Dementia. Jul. 2012, vol. 8, No. 4, p. 274, abstract P2-032.
O'Donovan Aoife et al. Stress appraisals and cellular aging: A key role for anticipatory threat in the relationship between psychological stress and telomere lenght. Brain Behav. Immun. May 2012, vol. 26, No. 4, pp. 573-579.
Tagawa Y et al: "Differences in spatial localization and chromatin pattern during different phases of cell cycle between normal and cancer cells", Cytometry, Alan Liss, New York, US, vol. 27, No. 4, Apr. 1, 1997 (Apr. 1, 1997), pp. 327-335.
Toland C F et al: "3D organisation of chromosome 11 centromeres in prostate cancer cell lines" Cellular Oncology vol. 27, No. 2, 2005, p. 158.
Aubele M et al: "Comparative fish analysis of numerical chromosome 7 abnormalities in 5-MUM and 15-MUM paraffin-embedded tissue sections from prostatic carcinoma" Histochemistry and Cell Biology, Springer, Berlin, DE, vol. 107, No. 2, Jan. 1, 1997 (Jan. 1, 1997), pp. 121-126.
Koutna I et al: "Topography of genetic loci in tissue samples: towards new diagnostic tool using interphase FISH and high-resolution image analysis techniques." Analytical Cellular Pathology : The Journal of the European Society for Analytical Cellular Pathology 2000, vol. 20, No. 4, 2000, pp. 173-185.
Solovei Irina et al: "Differences in centromere positioning of cycling and postmitotic human cell types" Chromosoma (Berlin), vol. 112, No. 8, Jun. 2004 (Jun. 2004), pp. 410-423.
Bayani Jane et al: "Spectral karyotyping identifies recurrent complex rearrangements of chromosomes 8, 17, and 20 in osteosarcomas." Genes Chromosomes and Cancer, vol. 36, No. 1, Jan. 2003 (Jan. 2003), pp. 7-16.
Beheshti et al: "Identification of a high frequency of chromosomal rearrangements in the centromeric regions of prostate cancer cell lines by sequential Giemsa banding and spectral karyotyping" Molecular Diagnosis, Naperville, IL, US, vol. 5, No. 1, Jan. 1, 2000 (Jan. 1, 2000), pp. 23-32.
Sarkar Rahul et al: "Alterations of centromere positions in nuclei of immortalized and malignant mouse lympocytes." Cytometry. Part A : The Journal of the International Society for Analytical Cytology Jun 2007, vol. 71, No. 6, Jun. 2007 (Jun. 2006), pp. 386-392.
Guffei Amanda et al: "c-Myc-dependent formation of robertsonian translocation chromosomes in mouse cells" Neoplasia (New York), vol. 9, No. 7, Jul. 2007 (Jul. 2007), p. 578.

(Continued)

*Primary Examiner* — Carla Myers
(74) *Attorney, Agent, or Firm* — Carmela De Luca; Bereskin & Parr LLP

(57) ABSTRACT

A method for diagnosing and/or evaluating dementia severity in a subject suspected of having or having dementia is provided the method comprising:
   a) obtaining a test cell sample from the subject,
   b) assaying the test cell sample to determine a telomere organization signature of the test sample, the telomere organization signature comprising one or more parameters selected from:
      i) telomere aggregates;
      ii) telomere number;
      iii) telomere length and telomere number;
      iv) telomere aggregates, telomere length and telomere numbers;
   c) comparing the test cell sample telomere organization signature to a control or one or more predetermined reference signatures; and
   d) diagnosing whether the subject has dementia and/or the dementia severity according to the test sample telomere organization signature.

13 Claims, 6 Drawing Sheets

(56) References Cited

OTHER PUBLICATIONS

Goncalves Dos Santos Silva Amanda et al: "Centromeres in cell division, evolution, nuclear organization and disease." Journal of Cellular Biochemistry Aug. 15, 2008, vol. 104, No. 6, Aug. 15, 2008 (Aug. 15, 2008), pp. 2040-2058.
Louis S F et al: "c-Myc induces chromosomal rearrangements through telomere and chromosome remodeling in the interphase nucleus" (2005) Proc. Natl. Acad. Sci USA. 102(27):9613-8.
Vermolen B J et al: "Characterizing the Three-Dimensional Organization of Telomeres" (2005) Cytometry A. 67A:144-50.
Mai S et al: "Oncogenic Remodeling of the Three-Dimensional Organization of the Interphase Nucleus" (2005) Cell Cycle. 4(10):1327-1331.
Mai S et al: "The Significance of Telomeric Aggregates in the Interphase Nuclei of Tumor Cells" (2006) Journal of Cellular Biochemistry. 97:904-15.
Beil M et al: "Spatial distribution patterns of interphase centromeres during retinoic acid-induced differentiation of promyelocytic leukemia cells" Cytometry. Apr. 1, 2002, vol.47, No. 4, pp. 217-225.
Beil M et al: "Statistical analysis of the three-dimensional structure of centromeric heterochromatin in interphase nuclei" J. Microsc. Jan. 2005, vol. 217, Pt. 1, pp. 60-68.
Garagna S et al: Three-dimensional localization and dynamics of centromeres in mouse oocytes during folliculogenesis. J. Mol. Histol. Aug. 2004, vol. 35, No. 6, pp. 631-638.
Kuroda M et al: Alteration of chromosome positioning during adipocyte differentiation. J. Cell Sci. Nov. 15, 2004, vol. 117, Pt 24, pp. 5897-5903.
Wiblin A E et al: Distinctive nuclear organisation of centromeres and regions involved in pluripotency in human embryonic stem cells. J. Cell Sci. Sep. 1, 2005, vol. 118, Pt 17, pp. 3861-3868.
Raz, Vered, et al., "Changes in lamina structure are followed by spatial reorganization of heterochromatic regions in caspase-8-activated human mesenchymal stem cells", Journal of Cell Science 119(20), Sep. 26, 2006, pp. 4247-4256.
Gonzalez-Suarez, Ignacio, et al., "Novel roles for A-type lamins in telomere biology and the DNA damage response pathway", The EMBO Journal (2009) 28, pp. 2414-2427.
Maierhofer, Christine et al. Multicolor Deconvolution Microscopy of Thick Biological Specimes. American Journal of Pathology. Feb. 2003, pp. 373-379.
Schaefer, L.H. et al. Generalized Approach for Accelerated Maximum Likelihood Based Image Restoration Applied to Three-dimensional Fluorescence Microscopy. Journal of Microscopy, Nov. 2001, vol. 204, No. Pt 2, pp. 99-107.
Henderson S. et al. In Situ Analysis of Changes in Telomere Size During Replicative Aging and Cell Transformation. The Journal of Cell Biology, Jul. 1996, pp. 1-12.
Bass, Hank W. et al. Telomeres Cluster de Novo Before the Initiation of Synapsis: A Three-dimensional Spatial Analysis of Telomere Positions Before and During Meiotic Prophase. Journal of Cell Biology, 1997, pp. 5-18, vol. 137, No. 1.
Weirich Claudia et al. Three-dimensional arrangements of Centromeres and Telomeres in Nuclei of Human and Murine Lymphocytes. Chromosome Research, 2003, pp. 485-502, vol. 11, No. 5.
Chuang Tony Chin Yuan et al. The three-dimensional organization of telomeres in the nucleus of Mammalian cells. BMC Biol. 2004, 2:12-20.
Lansdorp, Peter M. et al. Heterogeneity in telomere length of human chromosomes. Human Molecular Genetics, 1996, vol. 5, No. 5, pp. 685-691.
McDonald, J.H. Handbook of Biological Statistics. 2008, Excerpt of pp. 153-160.
Shapiro, D.E. The interpretation of diagnostic tests. Statistical Methods in Medical Research 8, 113-134, 1999.
Spitalnic, S. Test Properties 2: Likelihood Rations Bayes' Formula, and Receiver Operating Characteristic Curves. Hospital Physician 40, 53-58, 2004.
U.S. Cancer Statistics Working Group. United States Cancer Statistics: 1999-2009 Incidence and Mortality Web-based Report. Atlanta: U.S. Department of Health and Human Services, Centers for Disease Control and Prevention and National Cancer Institute; 2013. Available at: www.cdc.gov/uscs. Retrieved Sep. 10, 2013.
Kozubek, M. et al. Combined confocal and wide-field high-resolution cytometry of fluorescent in situ hybridezation-stained cells. Cytometry 45, 1-12, 2001.
Gehrke, I. et al. Three dimensional (3D) analysis of centromere organization in interphase nuclei of normal and tumor cells. AACR Meeting Abstracts 2005, 30 (2005).
Kozubek, M. et al. Automated acquisition and processing of multidimensional image data in confocal in vivo microscopy. Microscopy Research and Technique. 64, 164-175 (2004).
Thomas et al. Telomere length in white blood cells, buccal cells and brain tissue and its variation with ageing and Alzheimer's disease. Mechanisms of Ageing and Development, 129(4): 183-190, 2008.
Panossian et al. Telomere shortening in T cells correlates with Alzheimer's disease status. Neurobiology of Aging, 24(1): 77-84, 2003.
Jenkins et al. Increased "absence" of telomeres may indicate Alzheimer's disease/dementia status in older individuals with Down syndrome. Neuroscience Letter, 440(3): 340-343, 2008.
De Vos et al. Controlled light exposure microscopy reveals dynamic telomere microterritories throughout the cell cycle. Cytometry Part A, 75A: 428-439, 2009.
Lukens J. Nicholas et al. Comparisons of telomere lengths in peripheral blood and cerebellum in Alzheimer's disease. Alzheimer's & Dementia 5 (2009) 463-469.
Riudavits et al. Resistance to Alzheimer's pathology is associated with nuclear hypertrophy in neurons. Neurobiology of Aging, vol. 28, No. 10, Aug. 14, 2007, pp. 1484-1492.
D. M. Mann et al. Alterations in protein synthetic capability of nerve cells in Alzheimer's disease. Journal of Neurology Neurosurgery & Psychiatry., vol. 44, No. 2, Feb. 1, 1998, pp. 97-102.
Mathur Shuba et al. Three-dimensional quantitative imaging of telomeres in buccal cells identifies mild, moderate, and severe Alzheirmer's disease patients. Journal of Alzheimer's disease, vol. 39, No. 1, Jan. 1, 2014, pp. 35-48.
Statistical analysis of data performed in an Office Communication dated Sep. 9, 2013 in U.S. Appl. No. 12/443,781 entitled Methods of Detecting and Monitoring Cancer Using 3D Analysis of Centromeres.
Glogowska, Aleksandra et al. 10th International Conference on Alzheimer's and Parkinson's Disease. Conference, Barcelona, Spain, Mar. 9-13, 2011.
Francois, Maxime et al., Biomarkers of Alzheimer's Disease Risk in Peripheral Tissues; Focus on Buccal Cells. Current Alzheimer's Research, 2014, 11, 519-531.
McKhann M., Guy et al., The diagnosis of dementia due to Alzheimer's disease: Recommendations from the National Institute on Aging and the Alzheimer's Association workgoup. Alzheimer's & Dimentia (2011) 1-7.

* cited by examiner

METHODS FOR EVALUATING ALZHEIMER'S DISEASE AND DISEASE SEVERITY

CROSS REFERENCE TO RELATED APPLICATION

This application claims the benefit of 35 USC 119 based on the priority of U.S. Provisional Application No. 61/880,274 filed Sep. 20, 2013, which is herein incorporated by reference.

FIELD OF THE DISCLOSURE

The disclosure relates to methods for evaluating Alzheimer's disease and particularly to methods involving characterizing the organization of telomeres to diagnose and/or assess Alzheimer's disease occurrence and/or severity.

BACKGROUND OF THE DISCLOSURE

The ends of linear chromosomes are capped by telomeres. Human telomeres consist of repetitive two thymidine (TT), one adenine (A) and 3 glycine (GGG) subunits, which are associated with a variety of telomere-binding proteins known as the sheltering complex (Blackburn et al., 1994, de Lange et al., 2002).

Telomeres get progressively shorter with each cell division. This process occurs because the DNA-replication machinery is incapable of fully replicating the ends of linear molecules, and, degradation and oxidative damage of nucleotides in DNA. Telomerase is an enzyme, which has the ability to prevent telomeres from shortening although most of the cells do not express sufficient quantities of this enzyme to prevent this process. As a result, telomeres shorten with age in tissues and cells (Kenkichi et al., 2001, Harley et al., 2001, Huffman et al., 1990).

The function of telomeres is to mask and protect the ends of chromosomes from exposure to DNA damage. Telomeres maintain chromosome integrity. When telomere ends are unprotected, genomic instability is triggered. Genomic instability has been implicated as a major causal factor in cancer and aging (Charames et al., 2003, Holland et al., 2009, Hanialra et al., 2011).

Genomic instability is a crucial step in the development of most cancers. It has been suggested that inactivation of DNA repair pathways, which leads to an increased mutation rate and chromosomal instability, can initiate and accelerate the neoplastic process (Lothe et al., 1993, Rudolph et al., 1999, Colleu-Durel et al., 2001, Chan et al., 2002).

Genomic instability increases with age (Slagboom et al., 1999). There are a few potential mechanisms that have been proposed to explain age-dependent genome instability. These include the accumulation of oxidative damage to DNA, defects in mitochondrial functions that promote oxidative stress and DNA damage, mutations in proteins required for efficient DNA replication, DNA repair and checkpoints, telomere erosion and epigenetic effects on DNA repair and other genome maintenance programs (Hayflick et al., 1977, Sohal et al., 1985, Harley et al., 1990).

Telomeres become shorter during life. Accumulation of short telomeres in tissues contributes to pathological conditions such as congenital dyskeratosis, Werner premature aging syndrome and Alzheimer's disease (Yu et al., 1996, Shen et al., 1998, Fry et al., 1999, Burns et al., 2002, Panossian et al., 2003, Thomas et al., 2007).

Studies on telomere lengths in patients with Alzheimer's disease (AD) have revealed contrary results. Telomere shortening in AD seems to be cell type dependent (Panossian et al., 2003, Baird et al., 2004, Thomas et al., 2008). Short telomeres are found in cells such as lymphocytes, leukocytes, peripheral blood mononuclear cells, fibroblast cells, and buccal cells (BCs) from Alzheimer's patients (Jenkit et al., 2003, Panossian et al., 2003, Honig et al., 2006, Lukaset et al., 2009) whereas in brain tissue such as the hippocampus, telomeres have been found to be longer than in controls (Thomas et al., 2008). These findings indicate important differences in telomere maintenance in AD patients in different groups of cells.

AD is a neurodegenerative condition resulting in neuronal death. AD patients show symptoms of impaired memory, judgment and decision-making among other cognitive disabilities (Burns et al., 2002, Du et al., 2001). AD patients are currently diagnosed on clinical grounds while excluding other causes of dementia. The two histopathological structures present within the brain that positively identify AD conclusively at post-mortem are the neurofibrillary tangles and the amyloid-based neuritic plaques (Haroutunian et al., 1998, Matsson et al., 2000, Kawas et al., 2003).

Neurofibrillary tangles are composed of microtubule-associated hyperphosphorylated tau protein. Tau is associated with tubulin in the formation of microtubules. One function of microtubules is to provide points of attachment for chromosomes during cell division, which, if disrupted may result in an increased incidence of chromosome malsegregation and genomic instability (Iqbal et al., 1998, Petkova et al., 2002). The second histopathological feature of AD patients is the presence of amyloid-based neuritic plaques. 3-amyloid peptide (Aβ42) originates from the aberrant proteolysis of the amyloid precursor protein (APP) (Petkova et al., 2002, Antzutkin et al., 2002). The APP gene APP is located on chromosome 21. Aneuploidy of chromosomes 17 and 21 are common hallmarks of AD and genomic instability (Thomas et al., Mutagenesis 2008).

AD is an age related disease associated with genomic instability. Telomere shortening was studied in lymphocytes and fibroblasts in AD and age related healthy controls (Panossian et al., 2003, Cawthorn et al., 2003). A study by Thomas using PCR revealed a trend of shorter telomeres in AD samples compared to age matched controls (Thomas et al., 2008). Shorter telomeres were detected in peripheral blood mononuclear cells from AD patients (Honig et al., 2006, Thomas et al., 2008, Lukens et al., 2009).

SUMMARY OF THE DISCLOSURE

An aspect includes a method for evaluating and/or diagnosing a subject having or suspected of having Alzheimer's disease (AD) comprising:
  a) obtaining a test cell sample from the subject,
  b) assaying the test cell sample to determine one or more telomere organization signature of the test sample, the telomere organization signature comprising one or more parameter values selected from:
    i) telomere aggregates;
    ii) telomere number;
    iii) telomere length and telomere number; and
    iv) telomere aggregates, telomere length and telomere numbers;
  c) comparing the test cell sample telomere organization signature to a predetermined control or one or more predetermined reference signatures, d) evaluating and/or diagnosing whether the subject has AD and/or is likely to develop AD according to the test sample telomere organization signature.

In an embodiment, the control is a control reference value selected from: i) telomere aggregates; ii) telomere number; iii) telomere length and telomere number; and iv) telomere aggregates, telomere length and telomere numbers. In an embodiment, the one or more reference signatures each comprise one or more reference parameters values selected from: i) telomere aggregates; ii) telomere number; iii) telomere length and telomere number; and iv) telomere aggregates, telomere length and telomere numbers.

In an embodiment, the AD severity is evaluated.

In another embodiment, i) an increase in telomere aggregates, ii) an increase in telomere number to at least 65 per cell, iii) an increase in average cell telomere number and a decrease in telomere length, and/or iv) an increase in telomere aggregates, an increase in average cell telomere number and a decrease in telomere length in the test sample telomere organization signature compared to the reference telomere organization signature is indicative the subject has AD or an increased risk of developing AD and/or the severity of AD.

In an embodiment, the one or more parameter values comprises telomere aggregate number.

In an embodiment, the subject is diagnosed with AD when the average number of telomere aggregates is at least 3.5 per cell, 3.6 per cell, 3.7 per cell, 3.8 per cell, 3.9 per cell, 4.0 per cell, 4.1 per cell, 4.2 per cell, 4.3 per cell, 4.4 per cell or 4.5 per cell and/or the AD severity is diagnosed as moderate if the average number of telomere aggregates is at least 3.7 per cell, 3.8 per cell, 3.9 per cell, 4.0 per cell, 4.1 per cell, 4.2 per cell, 4.3 per cell, 4.4 per cell or 4.5 per cell and/or severe if the average number of telomere aggregates is at least 4.0 per cell, 4.1 per cell, 4.2 per cell, 4.3 per cell, 4.4 per cell or 4.5 per cell.

In an embodiment, the one or more parameter values comprises telomere number.

In an embodiment, a telomere number greater than 65 per cell, greater than 70 per cell, greater than 80 per cell, or greater than 85 per cell is indicative of AD or an increased likelihood of developing AD.

In an embodiment, a telomere number greater than about 65, about 70 or about 75 per cell is indicative of moderate AD and a telomere number greater than about 75, about 80 or about 85 per cell is indicative of severe AD.

In an embodiment, the one or more parameters is telomere length.

In an embodiment, telomere length is measured by determining relative fluorescent intensity and telomere lengths are grouped according to the following: (a) short telomeres where relative fluorescent intensity is less than 20,000 units, (b) mid-sized telomeres where relative fluorescent intensity is between 20,001-40,000 units and (c) long telomeres where relative fluorescent intensity is greater than 40,001 units and/or is measured in base pairs.

In an embodiment, a decrease in long telomeres and an increase in the proportion of short telomeres in the test sample telomere organization signature compared to the control or reference telomere organization signature is indicative of AD or an increased likelihood of developing AD.

In an embodiment, a decrease in telomere length of at least 200, at least 270, at least 300, at least 400, at least 500, at least 600, at least 700, at least 800, at least 900, at least 1000, at least 1100, at least 1200, at least 1300, at least 1400, at least 1480, at least 1500, at least 1600, at least 1700, at least 1800, at least 1900, at least 2000, at least 2100, at least 2200, at least 2300, at least 2340, at least 2400 or at least 2500 base pairs is indicative of AD or an increased likelihood of developing AD.

In an embodiment, a decrease of between about 200 and about 1000 base pairs is indicative of mild AD, a decrease of between about 1001 and about 2000 is indicative of moderate AD and a decrease of greater than about 2000 is indicative of severe AD In an embodiment, a decrease of about 10,000 AU, about 15,000 AU or less than 20,000 AU in maximum average telomere length and/or a maximum average telomere length of less than about 140,000 AU and greater than about 120,000 AU is indicative of mild AD.

In an embodiment, a decrease of about 20,000 AU, about 25,000 AU, less than 30,000 AU in maximum average telomere length and/or a maximum average telomere length of less than about 110,000 AU and greater than about 100,000 AU is indicative of moderate AD.

In an embodiment, a decrease of greater than about 30,000 AU, or greater than about 35,000 AU in maximum average telomere length and/or a maximum average telomere length of less than about 100,000 AU a is indicative of severe AD.

In an embodiment, the subject with AD or suspected of having AD is receiving treatment such as cholinesterase treatment. Current AD drugs are not disease modifying, and do not change the disease course.

The method can for example be used to test new therapies to assess if they are disease modifying.

In another aspect, the method is for assessing a putative treatment or monitoring a subject suspected of having or having AD receiving such treatment.

In an embodiment, the method comprises:
a) obtaining a first cell test sample from the subject,
b) obtaining a subsequent cell test sample from the subject,
c) assaying the first and second test samples to determine a first sample telomere organization signature and a subsequent cell sample telomere organization signature, each telomere organization signature comprising one or more parameters selected from:
  i) telomere aggregates;
  ii) telomere number;
  iii) telomere length and telomere number; and
  iv) telomere aggregates, telomere length and telomere numbers;
d) comparing the first test sample signature to the subsequent test signature, and
e) identifying the treatment as efficacious and/or the subject as progressing, stable or improving according to the differences or similarities between the first test sample signature and the subsequent test sample signature.

In an embodiment, the subject is administered a treatment after obtaining the first cell sample and before obtaining the subsequent cell sample.

In another embodiment, the method comprises:
a) obtaining a first test cell sample from the subject,
b) obtaining a subsequent test cell sample from the subject after the subject has received one or more treatments,
c) assaying the first and subsequent test cell sample to determine a first test cell sample telomere organization signature and a subsequent test cell sample telomere organization signature, each telomere organization signature comprising one or more parameters selected from:

i) telomere aggregates;
ii) telomere number;
iii) telomere length and telomere number; and
iv) telomere aggregates, telomere length and telomere numbers; and
d) comparing the first test cell sample telomere organization signature to the subsequent test cell sample telomere orgnaization signature, and
e) identifying differences or similarities between the first test cell sample telomere organization signature and the subsequent test cell sample telomere organization signature;

wherein a difference in the telomere organization of the subsequent test cell sample compared to the test cell sample obtained prior to the one or more treatments is indicative the subject is responding or not responding to the treatment.

In an embodiment, i) an increase in telomere aggregates, ii) an increase in telomere number to at least 65 per cell, iii) an increase in average cell telomere number and a decrease in telomere length, and/or iv) an increase in telomere aggregates, an increase in average cell telomere number and a decrease in telomere length in the subsequent test sample telomere organization signature compared to the first telomere organization signature is indicative the subject has worsening AD and/or is not responding to the treatment.

A further aspect includes a method for evaluating a subject suspected of having or having Alzheimer's disease (AD) comprising:
a) obtaining a test cell sample from the subject,
b) assaying the test cell sample to determine a telomere organization signature of the test sample, the telomere organization signature comprising one or more parameter values selected from:
i) telomere aggregates;
i) telomere number;
iii) telomere length and telomere number;
iv) telomere aggregates, telomere length and telomere numbers;
c) comparing the test cell sample telomere organization signature to a control or one or more predetermined reference signatures, and
d) evaluating and/or diagnosing whether the subject has AD and/or is likely to develop AD according to the test sample telomere organization signature.

In an embodiment, the control is a control reference value selected from: i) telomere aggregates; ii) telomere number; iii) telomere length and telomere number; and iv) telomere aggregates, telomere length and telomere numbers. In an embodiment, the one or more reference signatures each comprise one or more reference parameters values selected from: i) telomere aggregates; ii) telomere number; iii) telomere length and telomere number; iv) telomere aggregates, telomere length and telomere numbers.

In an embodiment, the Alzheimer's disease severity is evaluated.

In an embodiment, detecting i) an increase in telomere aggregates, ii) an increase in telomere number to at least 65 per cell, iii) an increase in average cell telomere number and a decrease in telomere length, and/or iv) an increase in telomere aggregates, an increase in average cell telomere number and a decrease in telomere length in the test sample telomere organization signature compared to the reference telomere organization signature is indicative the subject has Alzheimer's disease or an increased risk of developing Alzheimer's disease and/or the severity of Alzheimer's disease.

In an embodiment, the subject has Trisomy 21.

In an embodiment, the one or more predetermined reference signature parameter values is/are determined from a population of subjects that are known to be AD free, mild AD or moderate AD.

In an embodiment, the control is a threshold value associated with a population of subjects that are AD free.

In an embodiment, the reference signature is a threshold value associated with a population of subjects that have, mild, moderate or severe AD.

A further aspect includes a kit.

In an embodiment, the kit is for use in a method described herein comprising:
a sterile swab for collecting buccal cells; a receptacle for receiving the swab labelled with a unique identifier; and instructions of where to send the buccal cell swab sample for analysis.

In an embodiment, the kit comprises one or more of
a sterile collection swab for collecting a buccal cell sample;
a receptable for receiving the collection swab labelled with a unique identifier; and one or more of:
a microscope slide;
a fixative solution suitable for 3D preservation;
a wash solution;
a dehydration solution; and instructions for performing a method described herein.

In an embodiment, the sample comprises buccal cells.

In an embodiment, severity is mild Alzheimer's disease, moderate Alzheimer's disease or severe Alzheimer's disease.

In an embodiment, determining the telomere organization signature comprises quantitative fluorescence in situ hybridization (FISH), FISH for individual genes, chromosomes, chromosomal regions, centromeres, or immunocytochemistry, immunohistochemistry, histology or histochemistry.

In an embodiment, determining and/or characterizing the telomere organization signature comprises 3D analysis.

In yet another embodiment, the telomere organization signature is determined on interphase telomeres.

In an embodiment, determining the telomere signature comprises determining one or more of number of telomere aggregates, telomere numbers, and telomere lengths.

Optionally, the difference in telomere organization is telomere numbers and/or telomere length.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the disclosure will now be described in relation to the drawings in which.

DETAILED DESCRIPTION OF THE DISCLOSURE

Figure 1:
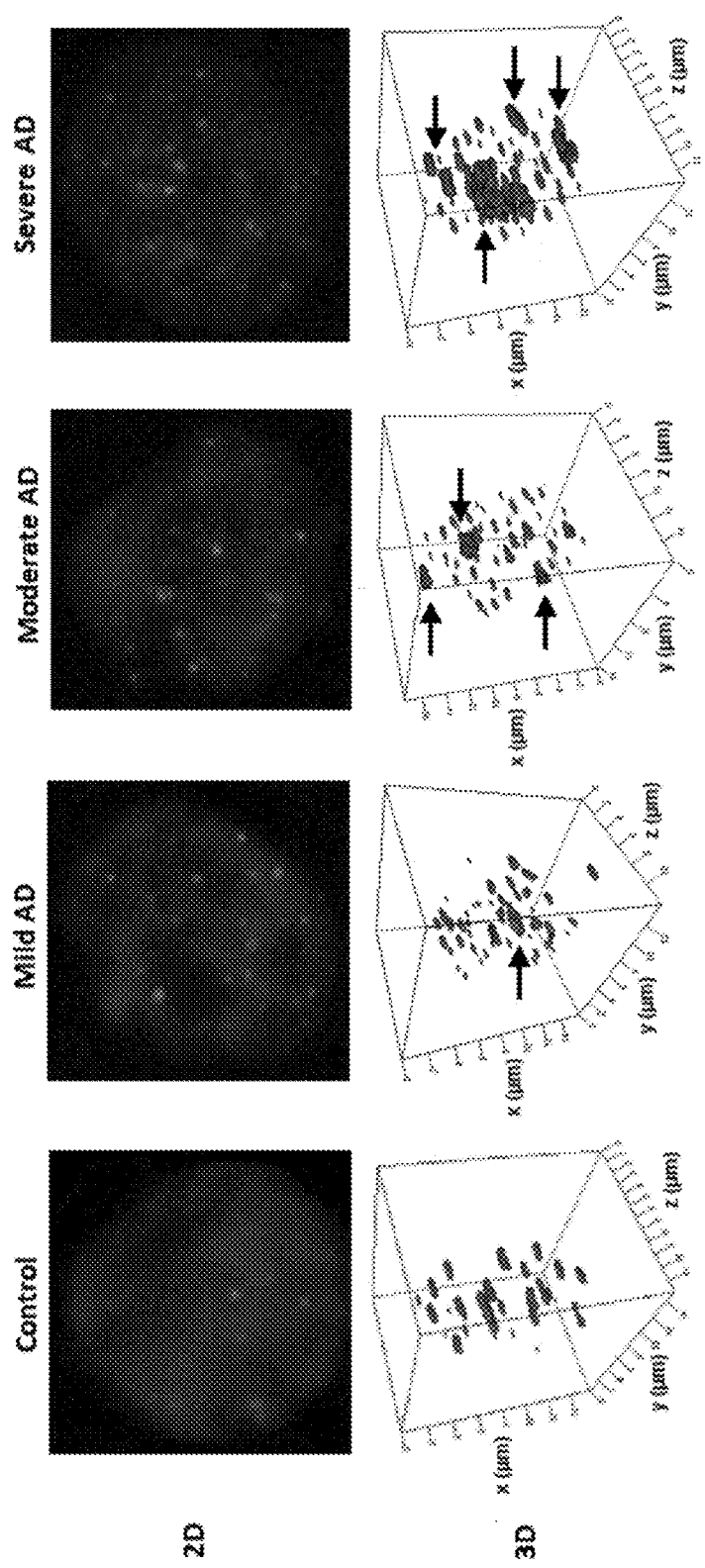
FIG. 1. 2D and 3D representative figures of nuclear telomeric architecture in buccal cells of Alzheimer patients and—matched cognitively normal caregivers. Images were acquired through an AxioImager Z2 microscope (Zeiss) (see Materials and Methods). 2D images show 4'6'-diamidino-2-phenylindole (DAPI) staining of the nucleus (darker grey) and PNA probe fluorescence (Cy3) staining of the telomeres (lighter grey spots). Each 2D maximum projection is complemented by its respective 3D telomere visualisation, illustrating the organization of the telomeres in the nuclei in the x, y and z dimensions. AD patients had shorter and visibly greater numbers of telomere signals (see Materials and Methods) in both 2D and 3D depictions in mild AD, moderate AD, and severe AD compared to controls. Telomere aggregation, defined as clusters of telomeres found in close proximity which cannot be further resolved as separate entities by TeloView at an optical resolution limit of 200 nm, are indicated by arrows, and were significantly increased in moderate and severe AD patients relative to controls (p=0.04; p=0.01, respectively). Significant increases in aggregation were also detected as AD progressed through the stages of mild to moderate, and moderate to severe AD (p=0.03; p=0.02, respectively).

The present disclosure will now be further described. In the following passages, different aspects are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

I. Definitions

The term "Alzheimer's disease" as is known in the art and used herein is a common form of dementia and is a neurodegenerative condition resulting in neuronal death wherein patients show for example symptoms of impaired memory, judgment and decision-making among other cognitive disabilities, wherein patients are diagnosed on clinical grounds while excluding other causes of dementia, and includes, mild, moderate and severe (e.g. advanced) AD. Diagnosis presently involves a comprehensive evaluation such as a complete health history, physical examination, neurological and mental status assessments, analysis of blood and urine, electrocardiogram, and possibly an imaging exam, such as CT or MRI. The two histopathological structures present within the AD brain are neurofibrillary tangles and the amyloid-based neuritic plaques (Haroutunian et al., 1998, Matsson et al., 2000, Kawas et al., 2003).

"Mild AD" as used herein in reference to a patient means for example a patient with a Montreal Cognitive Assessment (MoCA) test (Nasreddine et al., 2005) score above 18/30; "Moderate AD" refers to for example a patient with a Mini-Mental State Exam (MMSE) (Folstein et al., 1975) score between 16/30 and 21/30 (inclusive); and "Severe AD" or "Advanced AD" which are used interchangeably, refers for example to a patient with an MMSE score <16/30. Other comparable grading scales can also be used.

The term "buccal cells" or "BCs" as used herein means cells in the mouth cavity including for example buccal epithelial cells from the inside of the cheek.

The term "control" as used herein means any tissue, biological fluid or cell sample from one or more subjects not having Alzheimer's disease (AD) (e.g. control subjects) such as an age matched control or can be a reference value (e.g. a reference parameter value) derived from such samples corresponding to a telomere organization parameter (e.g. determined from a sample from a control subject or group of control subjects).

The term "reference value" as used herein is a suitable comparator such as a threshold or cut off value, for example corresponding to the number of telomere aggregates or number of telomeres, above which is associated with AD, or a telomere length, below which is associated with AD. In embodiments where the severity of AD is being compared, the reference value can be a disease reference value for example mild AD reference value, moderate AD reference value or severe AD reference value, wherein a value such as a threshold value is determined for a population of subjects having similar disease e.g. mild AD, moderate AD or severe AD. As an example, a subject with telomere parameters such as a decrease in length or increase in number (aggregates or telomere numbers) compared to for example the mild AD reference value is identified as having moderate or severe AD. The reference value can be a value arising from population studies, theoretical models, or the characterization of control cells.

The term "age matched control" as used herein means a control that is within 15 years, 10 years, 5 years or 1 year of the test subject.

The term "sex matched control" as used herein means a control that is the same gender as the test subject.

The phrase "characterizing telomeric organization of cells" as used herein means the application of a method comprising an algorithm to image data to determine at least one parameter of the telomeric organization, or optionally acquiring image data and the application of a method comprising an algorithm to image data to determine at least one parameter of the telomeric organization.

The phrase "determining telomeric organization of cells" as used herein means the application of a method to a sample which results in identifying at least one parameter that characterizes the telomeric organization. For example, parameters include telomere number, number of telomere aggregates, and telomere length. The terms refer to the average per cell of a plurality of cells.

The term "sample" as used herein means any tissue, biological fluid or cell sample comprising chromosomal DNA containing cells (e.g. test cells) from a subject, including for example buccal cells. The sample can also comprise brain tissue for example collected post mortem. The sample can be processed using methods known in the art. For example, buccal cells can be obtained by buccal swab using sterile swabs, smearing the buccal cells on microscope slides and storing the samples frozen and/or fixed, optionally using formaldehyde and stored, for example at −20° C., until ready for processing.

As used herein, the term "cell" includes more than one cell or a plurality of cells or portions of cells. The term "test cell" is a cell from a subject that is suspected of having Alzheimer's disease. The term "control cell" is a suitable comparator cell e.g. a cell that is an age matched control. In one embodiment, a "test cell sample" comprises at least 5, 10, 15, 20, 25, 30, 40 or 50 cells.

The term "subject" as used herein refers to any member of the animal kingdom, preferably a human being.

The term "three dimensional (3D) analysis" as used herein means any technique that allows the 3D visualization and/or image analysis of cells, for example high resolution deconvolution microscopy, and can include one or more of 3D microscopy, image restoration or deconvolution, visualization and image analysis. An example of 3D image analysis is provided in Vermolen et al., 2005, which is incorporated herein by reference, and U.S. Pat. No. 7,801,682, issued Sep. 21, 2010 titled Method of Monitoring Genomic Instability Using 3D Microscopy and Analysis, which is also herein incorporated by reference.

The term "two dimensional (2D) analysis" as used herein means any technique that allows the 2D visualization and/or image analysis of cells, such as 2D microscopy and can include one or more of 2D microscopy, visualization and image analysis.

The terms "telomeric organization" and/or "telomere organization" as used herein refers to the 3D arrangement of the telomeres during any phase of a cell cycle and includes such parameters as alignment (e.g. nuclear telomere distribution), number of telomere aggregates, telomere numbers and/or telomere sizes, a/c ratios and/or nuclear volumes. For example, fluorescent intensity is proportional to telomere size. Telomere size can be assessed by measuring fluorescent units (which are arbitrary units) as is demonstrated in the graphs of mild, moderate and severe AD compared to controls or by calculating base pairs as described below. The parameters are per cell for a plurality of cells. For example, telomeres with a relative fluorescent intensity (x-axis) ranging from 0-20,000 units are classified as short, with an intensity from 20,001-40,000 units as mid-sized, and with an intensity >40,001 units as large. Mid and large size telomeres can also be grouped together for example >20,001 units. "Telomeric organization" also refers to the size and shape of the telomeric disk, captured for example in an a/c ratio and which is the organized structure formed when the telomeres condense and align during the late G2 phase of the cell cycle.

The term "number of telomere aggregates" refers to the presence or absence of telomere aggregate(s) and/or the number of aggregates of telomeres. As an example, telomere aggregates are defined as clusters of telomeres that are found in close association and cannot be further resolved as separate entities at an optical resolution limit of for example 200 nm (63× oil) and 350 nm (40×).

The term "telomere organization signature" as used herein refers to one or a plurality of values each value corresponding to a telomere organization parameter selected from number of telomere aggregates, telomere number, telomere length, telomere nuclear volume and telomere a/c ratio, optionally i) telomere aggregate number, ii) telomere number, iii) telomere length and telomere number, or iv) telomere aggregate number, telomere length and telomere number—of a cell or average of a group of cells for example at least 5 cells, a least 10 cells, at least 15 cells, at least 20 cells, at least 25 cells or at least 30 cells of a cell sample. The values can include a statistical measure and/or can be a range or threshold and can be used to classify the cell sample for example as normal or aberrant; Alzheimer's or non-Alzheimer's; progressing or stable; responsive to treatment or non-responsive to treatment, when compared to a control or a reference signature. The criteria that define the differences include such parameters as alignment (e.g. nuclear telomere distribution), number of telomere aggregates, telomere numbers per cell and/or telomere sizes, a/c ratios and/or nuclear volumes. The telomere organization signature can be of a test cell sample or a reference telomere organization.

The term "test cell sample telomere organization signature" as used herein refers to a telomere organization signature obtained from a cell or group of cells in a test sample, for example a cell or sample from a subject that is suspected of having Alzheimer's disease or a risk of having Alzheimer's disease.

The term "reference telomere organization signature" as used herein refers to a telomere organization signature corresponding to or derived from a group of samples and associated with a control population, disease population or disease severity and comprises values for a plurality of telomere organization parameters. For example, a reference telomere organization signature is optionally obtained from a cell sample from a subject or group of subjects that is known as not having Alzheimer's disease or a risk of having Alzheimer's disease or that is known as having Alzheimer's disease, such as mild, moderate or severe AD.

The term "telomere length" as used herein refers to the relative fluorescent intensity of telomeres that corresponds to the physical length of telomeric DNA and/or the base pair length of telomeres. For example, telomeres with a relative fluorescent intensity (x-axis) ranging from 0-20,000 units are classified as short, with an intensity from 20,001-40,000 units as mid-sized, and with an intensity >40,001 units as large (Knecht H, Sawan B, Lichtensztejn Z, Lichtensztejn D, Mai S. Lab Invest. 2010; 90(4):611-619). The length of telomeric DNA in base pairs, can be calculated using of certain techniques. For example, it has been shown that the PNA probe hybridizing to the telomeric end is directly proportional to the length of the telomeric DNA. The relative fluorescent telomeric signal intensity represents the length of the telomeres in arbitrary units. Subsequently, the base pair length can be computed from this intensity in order to evaluate telomere length. This can be calculated through a conversion factor derived from cells such as Raji cells, a Burkitt's lymphoma cell line used as a control. Any cell line with a defined telomere length can be used in the determination of a conversion factor. Once Raji cells are harvested, half are used for telomere restriction fragment (TRF) analysis via Southern blot while the rest undego PNA Q-FISH using identical conditions as set for AD buccal cells. Using TeloView, an average telomere intensity is calculated for the Raji cells. This correlates with the telomere length resulting from the TRF analysis, thus deriving the conversion factor. The average intensities of AD buccal cells are then converted into base pairs using this conversion factor.

The term "short telomeres" as used herein means telomeres with a relative fluorescent intensity (x-axis) ranging from 0-20,000 units which are classified as short, the term "mid-sized telomeres" as used herein means telomeres with a relative fluorescent intensity (x-axis) ranging from 20,001-40,000 units which are classified as mid-sized and "large telomeres" as used herein means telomeres with a relative fluorescent intensity (x-axis) of >40,001 units which are classified as large.

The term "difference or similarity in telomere organization between the sample and the control and/or in the test cell compared to the control cell" or "differences or similarities between the test sample signature and the one or more control reference signatures" can be determined, for example by counting the number of telomeres in the cell, measuring the size or volume of any telomere or telomere aggregate, or measuring the alignment of the telomeres, and comparing the measured values between the cells in the sample and the cells in the control or reference signature value. The differences in telomeric organization between the sample and the control can be measured and compared using individual cells or average values from a population of cells. The telomeres in a test cell may also be fragmented and therefore appear smaller than those in the control cell. Accordingly, a change or difference in telomeric organization in the test cell compared to the control cell can be determined by comparing parameters used to characterize the organization of telomeres. Such parameters are determined or obtained for example, using a system and/or method described herein below.

The term "a/c ratio" as used herein describes the level to which the volume occupied by the telomeres is oblate. The larger it is, the more oblate (or disklike) is the shape of the volume occupied by the telomeres, while a/c=1 means that this volume is spherical.

The term "nuclear volume" as used herein means the volume of a cell nucleus. Nuclear volume can be calculated according to the 3D nuclear 4',6-diamidino-2-phenylindole staining (DAPI) protocol described in Vermolen B J et al., (2005).

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a" "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

II. Methods

It is demonstrated herein using 3D analysis that the number of telomere aggregates and the number of telomeres is increased and that the lengths of telomeres are decreased in subjects with Alzheimer's disease compared to healthy controls. It is demonstrated for example that the changes in telomere aggregate numbers, telomere numbers and telomere lengths can differentiate between AD patients and controls and patients with mild, moderate and severe forms of AD.

As telomere numbers and telomere aggregates continue to increase and telomere length continues to reduce with progressive AD, it would seem predictable that a subject that has one or more of these features such as increased telomere numbers and decreased telomere lengths, but which does not meet the criteria for AD, for example using a mental exam, is at risk of developing AD (e.g. according to presently defined criteria).

Figure 5:
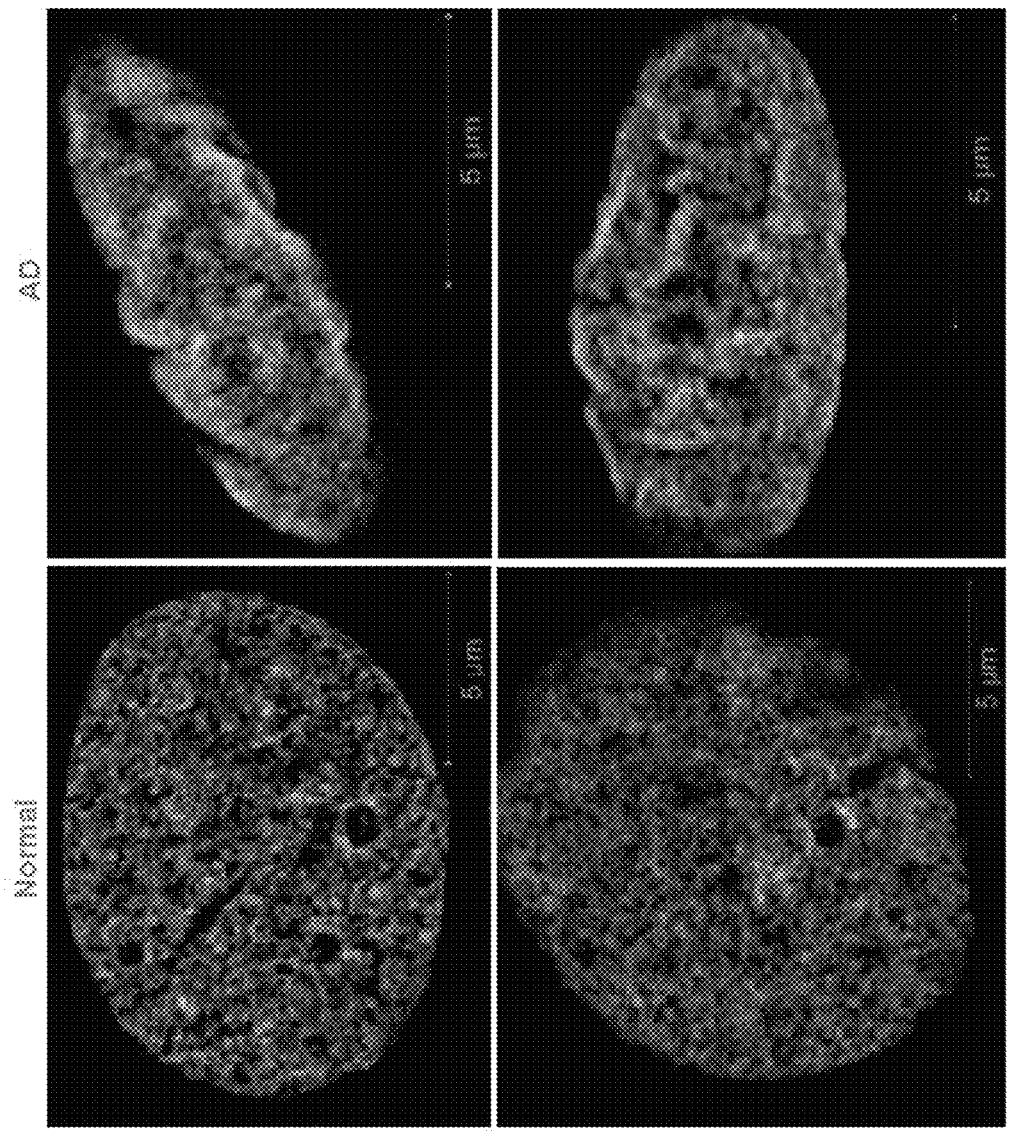
FIG. 5. 3D Structured illumination microscopy. 3D Structured illumination microscopy (3D-SIM) (see Methods and Materials in Example 1) was utilized in order to visualize whether changes in nuclear organization of buccal cells in AD patients occurred relative to normal age and sex-matched controls. Representative cells from two normal and two severe AD patients are shown. Comparatively, cells of severe AD patients showed extensive morphological changes. Although the cause is unknown, this chromatin reorganization may partially attribute to the increase in telomere number and decrease in length found in AD patients.

As shown in FIG. 5, there is an amazing difference in the 3D nuclear organization of samples from subjects with AD compared to subjects which is only seen with super resolution microscopy. FIGS. 5 a) and b) show DAPI-stained cells (e.g. a DNA stain) allowing appreciation of the irregular nature of the AD buccal cells as opposed to the controls. This suggests nuclear remodeling of the chromatin and its organization in AD.

3D nuclear imaging analysis is a sensitive technique and as demonstrated herein can be used to measure not only telomere length but also telomere aggregate numbers and/or telomere numbers in buccal cells. The methods described for example permit more parameters to be assessed providing more comprehensive diagnostic characteristic, including nuclear volume and a/c ratio. In addition, as 3D analysis is very sensitive, diagnostic accuracy is improved.

Accordingly, an aspect includes a method for evaluating and/or diagnosing a subject having or suspected of having AD comprising:
  a) assaying a test cell sample to determine one or more telomere organization signature of the test sample, the telomere organization signature comprising one or more parameter values selected from:
  i) telomere aggregates;
  ii) telomere number;
  iii) telomere length and telomere number; and
  iv) telomere aggregates, telomere length and telomere numbers;
  c) comparing the test cell sample telomere organization signature to a control and/or one or more predetermined reference signatures;
  and
  d) evaluating and/or diagnosing whether the subject has AD and/or is likely to develop AD according to the test sample telomere organization signature.

In an embodiment, the control is a control reference value selected from: i) number of telomere aggregate; ii) telomere number; iii) telomere length and telomere number; and iv) telomere aggregates, telomere length and telomere numbers.

Where the control is a reference value, comparing the test cell sample telomere organization signature to a control comprises calculating a value for i) number of telomere aggregates; ii) telomere number; iii) telomere length and telomere number; and
  iv) telomere aggregates, telomere length and telomere numbers and comparing it to the reference value. If the per cell number of telomere aggregates or telomere numbers is increased in the test sample compared the reference signature, the subject has or has an increased risk of developing AD. Alternatively, if the per cell average length of telomeres, for example measured in base pairs, or if the per cell average length of a telomere length sub-group such as short, mid or large telomeres is reduced compared to the reference value, he subject has or has an increased risk of developing AD.

Where the parameters chosen comprise 2 parameters such as telomere length an telomere number, and the control is a reference value, each of the parameters is compared to a reference value, e.g. a reference value for telomere length and telomere number. A test sample that comprises at least one parameter selected from number of telomere aggregates and number of telomeres that is increased compared the control reference value, and/or a telomere length that is decreased compared to a control is in an embodiment, indicative that the subject has AD and/or an increased likelihood of developing AD. In an embodiment, at least two or all three parameters exhibit increases/decreases associated with AD In an embodiment, the one or more reference signatures each comprise one or more reference parameters values selected from: i) telomere aggregates; ii) telomere number; iii) telomere length and telomere number; and iv) telomere aggregates, telomere length and telomere numbers.

Comparing a test cell sample telomere organization to one or more reference signatures can comprise comparing more one or more than one parameter and assessing if one or more parameters is most likely to fall with the range of values associated with AD or controls, or mild, moderate or severe AD. For example, TeloView™ and/or TeloScan™ can be used.

In an embodiment, a sample is obtained from the subject. The sample is processed and prepared for imaging and characterizing the telomere organization for example as described herein.

In an embodiment, the AD severity is evaluated.

In an embodiment, the severity is optionally mild Alzheimer's disease, moderate Alzheimer's disease or severe Alzheimer's disease.

A difference in telomere organization is found for example when at least one parameter of the telomere organization signature of the sample cell is different compared to the reference signature. Accordingly, in one embodiment, the method comprises:
  a) determining a telomere organization signature of a test cell sample from the subject, determining the telomere organization signature comprising determining one or more of telomere numbers, telomere lengths and number of telomere aggregates of the test cell sample, and
  b) comparing the telomere organization signature of the test cell sample with a reference telomere organization signature, the reference signature comprising reference values for one or more of telomere numbers, telomere length and number of telomere aggregates;
  wherein an increase in the telomere numbers and/or number of telomere aggregates and/or a decrease in telomere length in the test sample telomere organization signature compared to the reference telomere organization signature is indicative the subject has Alzheimer's disease or an increased risk of developing Alzheimer's disease.

Figure 3:
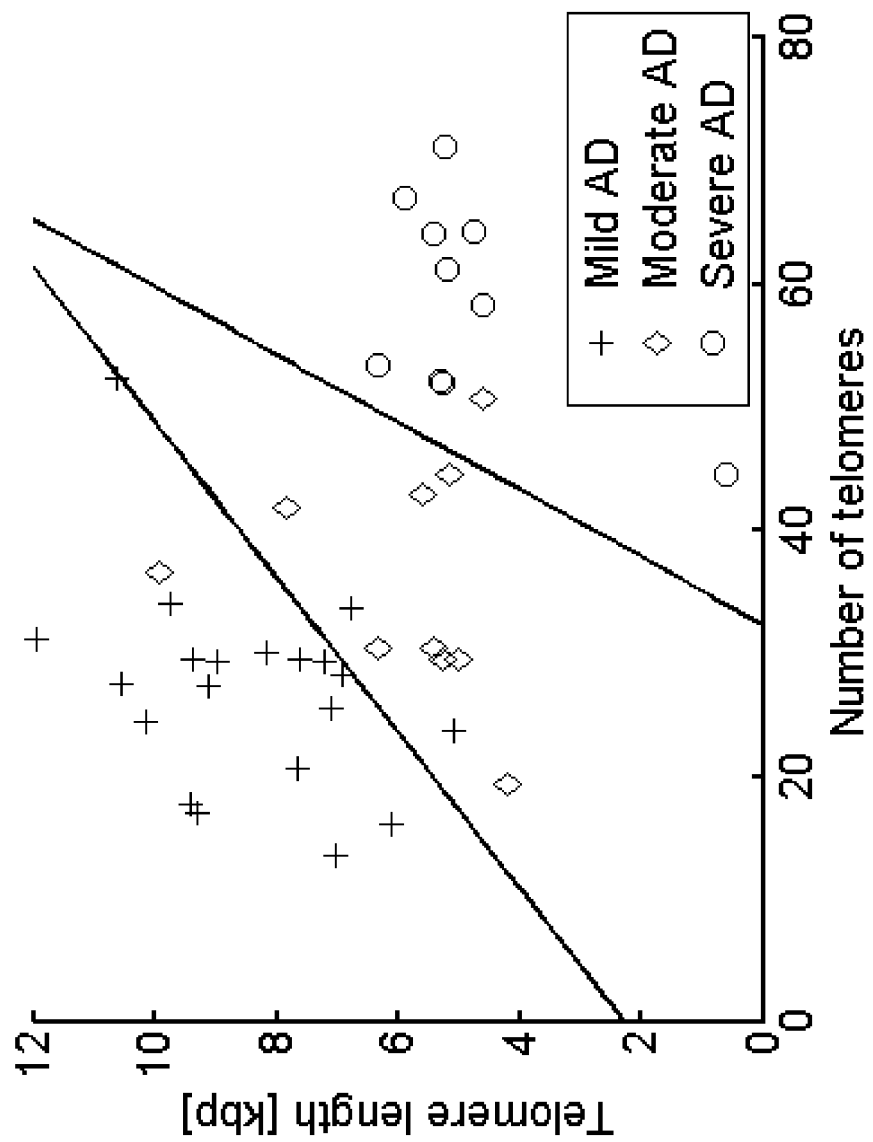
FIG. 3. Classification scatterplot of mild, moderate and severe AD patients (N=41). The average number and length of detected telomeres for each patient with mild AD (crosses), moderate AD (diamonds) and severe AD (circles) are illustrated. Linear classification boundaries are depicted with black lines, showing most errors occurred close to these boundaries. This classification had a 9.8% error rate after normalization to equal probability of each stage. See text and Table 2 for more details.

In an embodiment, the parameters comprise telomere number and telomere length. Two parameters can for example be plotted to identify disease severity. As described in the Examples, in order to discriminate between AD profiles, the telomere numbers were plotted against the length for each of the 41 AD patients. Using TeloView, the patients fell into the three severity groups with minor overlap (see FIG. 3 of paper). FIG. 3 describes the ranges where the majority of telomeric signals were detected. Subsequently, the space was divided into three parts corresponding to each of the levels of AD severity. This classification had a 9.8% error rate after normalization to equal probability of each AD stage. The 9.8% error rate may represent differences between the cognitive assessment and the quantitative measurements of TeloView.

The exact number of errors is shown in the confusion matrix in Table 2.

In another embodiment, the method comprises:
  a) determining a telomere organization signature of a test cell sample from the subject, determining the telomere organization signature comprising determining one or more of telomere numbers and telomere lengths of the test cell sample, and b) comparing the telomere organization signature of the test cell sample with a reference telomere organization signature, the reference signature comprising reference values for one or more of telomere numbers and telomere length;

wherein an increase in the telomere numbers and/or a decrease in telomere length in the test sample telomere organization signature compared to the reference telomere organization signature is indicative the subject has Alzheimer's disease or an increased risk of developing Alzheimer's disease.

In another embodiment, the method comprises:

a) determining a telomere organization signature of a test sample from the subject, determining the telomere organization signature comprising determining number of telomere aggregates of the test cell sample, and b) comparing the telomere organization signature of the test cell sample with a reference telomere organization signature, the reference signature comprising reference values for number of telomere aggregates;

wherein an increase in the number of telomere aggregates n the test sample telomere organization signature compared to the reference telomere organization signature is indicative the subject has Alzheimer's disease or an increased risk of developing Alzheimer's disease.

In an embodiment, determining the telomere organization comprises determining telomere numbers, telomere length and number of telomere aggregates.

In one embodiment, the method comprises (a) determining a telomere organization signature of a test cell sample from a subject suspected of having or having Alzheimer's disease, determining the telomere organization comprising determining one or more of telomere numbers, telomere length and number of telomere aggregates, and (b) detecting one or more of an increase in the telomere numbers abd number of telomere aggregates, a decrease in telomere length in the test cell sample telomere organization signature compared to the reference telomere organization signature.

In yet another embodiment, the methods described herein are applied to a subject with AD.

In an embodiment, determining the telomeric organization in the test sample cells and/or control comprises using quantitative fluorescence in situ hybridization (quantitative FISH or Q-FISH). For example, sample cells can be hybridized using a telomere PNA FISH probe. Digital images of the hybridized cells can for example be taken using a Zeiss Axiolmager and images can be acquired for example by Axiovision (Zeiss) followed by constrained iterative deconvolution as described below and for example in Example 1. In an embodiment, determining and/or characterizing the telomeric organization in the test cell comprises using three dimensional (3D) analysis. Examples of 3D analysis are described below and in Vermolen et al 2005 and below.

In an embodiment, the FISH can be FISH for individual genes, chromosomes, chromosomal regions, cetnromeres.

In another embodiment, determining the telomeric organization in the test sample comprises immunocytochemistry, immunohistochemistry, histology and histochemistry.

A difference in telomeric organization is found for example when at least a parameter of the 3D organization is different compared to control cells. In an embodiment, the difference is an increased number of telomeres in the test sample cells compared to a control. In another embodiment, the difference is a decrease in the length of telomeres in the test sample cells compared to a control. For example, where the control is a healthy control, an increase in the number of telomeres and decrease in the length of telomeres is indicative the subject has Alzheimer's disease or an increased risk of developing Alzheimer's disease. The length of telomeres can for example be the average length of telomeres in a cell, or a number of cells. In an embodiment, the number of cells assessed is sufficient for statistical analysis. For example, at least 5 cells, 10 cells, 15 cells, 20 cells, 25 cells or 30 cells are analyzed for telomeric organization. The statistical tests that can be employed include for example Chi square test for telomere length, and Fisher's exact test for telomere numbers. ANOVA can also be used. In an embodiment, the statistical test used is a Student T test. In an embodiment, the increase (or decrease) is a statistically significant increase (or decrease). The increased risk for example can be expressed as an odd's ratio.

It is demonstrated for example that subjects with Alzheimer's disease have significant differences in short (e.g. low intensity), mid-sized (e.g. mid intensity) and large (high intensity) telomeres compared to normal and also according to severity of disease (e.g. mild, moderate and severe AD).

Low intensity is for example considered to be 0-20,000K relative fluorescent units, mid intensity is for example considered to be 20,001-40,000 relative fluorescent units and high intensity is considered to be >40,001 relative fluorescent units. Using these intensities, mild AD is significantly different from normal age-matched controls, and from moderate or severe AD.

Detecting one or more of an increase in the telomere numbers and/or number of telomere aggregates, and a decrease in telomere length in the test cell sample telomere organization signature compared to the reference telomere organization signature is for example indicative of Alzheimer's disease or an increased likelihood of developing Alzheimer's disease.

In an embodiment, the telomere number associated with AD is for example, greater than 60 per cell, greater than 65 per cell, greater than 70 per cell, greater than 75 per cell, greater than 80 per cell, greater than 85 per cell or greater than 90 per cell.

In an embodiment, the telomere number associated with moderate AD is about 65 to about 85 per cell and advanced AD, greater than 85 per cell.

In an embodiment, the decrease in telomere intensity and/or decrease base pairs associated with AD is at least 10%, at least 20%, at least 30%, at least 50% decreased compared to a control or reference value. The decrease is optionally in telomeres having a fluorescence intensity within 0-20000 Units, 20001-40000 units and/or greater than 40001 units. Typically decreases in all three ranges are documented. In an embodiment, the decrease in telomere intensity associated with mild AD is at least 10%, or at least 20% decreased compared to control. In an embodiment, the decrease in telomere intensity associated with moderate AD is at least 10%, at least 20% or at least 30% decreased compared to control. In an embodiment, the decrease in telomere intensity associated with advanced AD is at least 10%, at least 20%, at least 30% or at least 40% decreased compared to control or reference value.

In an embodiment, a decrease of about 10,000 AU, about 15,000 AU or less than 20,000 AU in maximum average telomere length and/or a maximum average telomere length of less than about 140,000 AU and greater than about 120,000 AU is indicative of mild AD.

In an embodiment, a decrease of about 20,000 AU, about 25,000 AU, less than 30,000 AU in maximum average telomere length and/or a maximum average telomere length of less than about 110,000 AU and greater than about 100,000 AU is indicative of moderate AD.

In an embodiment, a decrease of greater than about 30,000 AU, or greater than about 35,000 AU in maximum average telomere length and/or a maximum average telomere length of less than about 100,000 AU a is indicative of severe AD.

Telomere length shortened with increasing AD severity. For example, it is demonstrated herein that subjects with mild AD had telomeres that were 7240 bp+/−1300 whereas controls had telomeres that were 7510 bp+/−1140; subjects with moderate AD had telomeres that were 5960 bp+/−1080 whereas controls had telomeres that were 7440+/−1620; and subjects with severe AD had telomeres that were 5480 bp+/−1070 compared to controls which had telomeres that were 7820 bp+/−1640.

The control can for example be a threshold where in which subjects with a number of telomeres and/or aggregates above the threshold and length of telomeres below the threshold are indicated as having Alzheimer's disease or an increased risk of Alzheimer's disease.

In an embodiment, the test sample comprises buccal cells. In another embodiment, the test sample is brain tissue, for example collected post mortem.

In an embodiment, the Alzheimer's disease is mild Alzheimer's disease. In another embodiment, the Alzheimer's disease is moderate Alzheimer's disease. In yet another embodiment, the Alzheimer's disease is severe Alzheimer's disease.

As the telomeric alterations seen in samples increased with disease severity, the methods described herein can also be used to assess disease severity and/or assess putative AD therapies and/or monitor disease in a subject receiving such therapy.

In an embodiment, the control reference value is a subject with mild AD. In another embodiment, the disease control is a subject with moderate AD.

A method for assessing a putative AD treatment and/or monitoring a subject suspected of having or having AD comprising receiving such treatment:
a) obtaining a first cell test sample from the subject,
b) obtaining a subsequent cell test sample from the subject,
c) assaying the first and second test samples to determine a first sample telomere organization signature and a subsequent cell sample telomere organization signature, each telomere organization signature comprising one or more parameters selected from:
   i) telomere aggregates;
   ii) telomere number;
   iii) telomere length and telomere number;
   iv) telomere aggregates, telomere length and telomere numbers;
d) comparing the first test sample signature to the subsequent test signature, and
e) identifying the treatment as efficacious and/or the subject as progressing, stable or improving according to the differences or similarities between the first test sample signature and the subsequent test sample signature.

In an embodiment, the method comprises:
a) obtaining a sample comprising cells from the subject; and
b) determining and/or characterizing the telomeric organization of cells in a test sample from the subject;
wherein a difference in the telomeric organization of the test sample cells compared to a previous sample is indicative the subject has progressing Alzheimer's disease and/or ameliorating Alzheimer's disease and a lack of difference in the telomeric organization of the test sample cells compared to a previous sample is indicative of stable Alzheimer's disease.

The method can also be used to monitor treatment therapy. In an embodiment, the method comprises:
a) determining and/or characterizing the telomeric organization of cells in a test sample from the subject after the subject has received one or more treatments;
wherein a difference in the telomeric organization of the test sample cells compared to a sample obtained prior to the one or more treatments is indicative the subject is responding or not responding to the treatment.

For example, if a sample obtained after treatment indicates that the cell telomere lengths decreased and/or numbers are increased (e.g. telomere number and/or number of aggregates) compared to the sample obtained prior to the one or more treatments, the subject is predicted to not be responding to treatment. If the telomere lengths and/or numbers are stabilized and/or telomere lengths are increased and/or numbers are decreased, the subject is predicted to be responding to the treatment.

In an embodiment the telomere organization is determined for interphase telomeres.

Also provided is use of the methods described for selecting a treatment, wherein a subject is monitored for response to a treatment and treatment is continued if responding or a new treatment is selected if not responding.

The methods can also be used for example to differentiate subjects in clinical trials testing new therapies.

In an embodiment, an automated method is used for example Teloscan™ (Klewes et al 2011).

a) Method of Characterizing 3D Organization of Patient Samples

Methods and systems for determining the 3D organization of telomeres are described in U.S. Pat. No. 7,801,682, issued Sep. 21, 2010 titled Method of Monitoring Genomic Instability Using 3D Microscopy and Analysis, which is incorporated herein by reference in its entirety. An automated method that can be used is Teloscan™ described in Klewes et al 2011, incorporated herein by reference in its entirety.

In an embodiment the method for characterizing a 3D organization of telomeres comprises:
(i) inputting image data of the 3D organization of telomeres;
(ii) processing the image data using an image data processor to find a set of coordinates $\{(x_i, y_i, z_i)\}$, i=1, . . . , N, where $(x_i, y_i, z_i)$ is a position of the ith telomere;
(iii) finding a plane that is closest to the set of coordinates; and
(iv) finding a set of distances $\{d_i\}$=1, . . . , N, where $d_i$ is the distance between $(x_i, y_i, z_i)$ and the plane, wherein the set $\{d_i\}$ is utilized to characterize the 3D organization.

Figure 6:
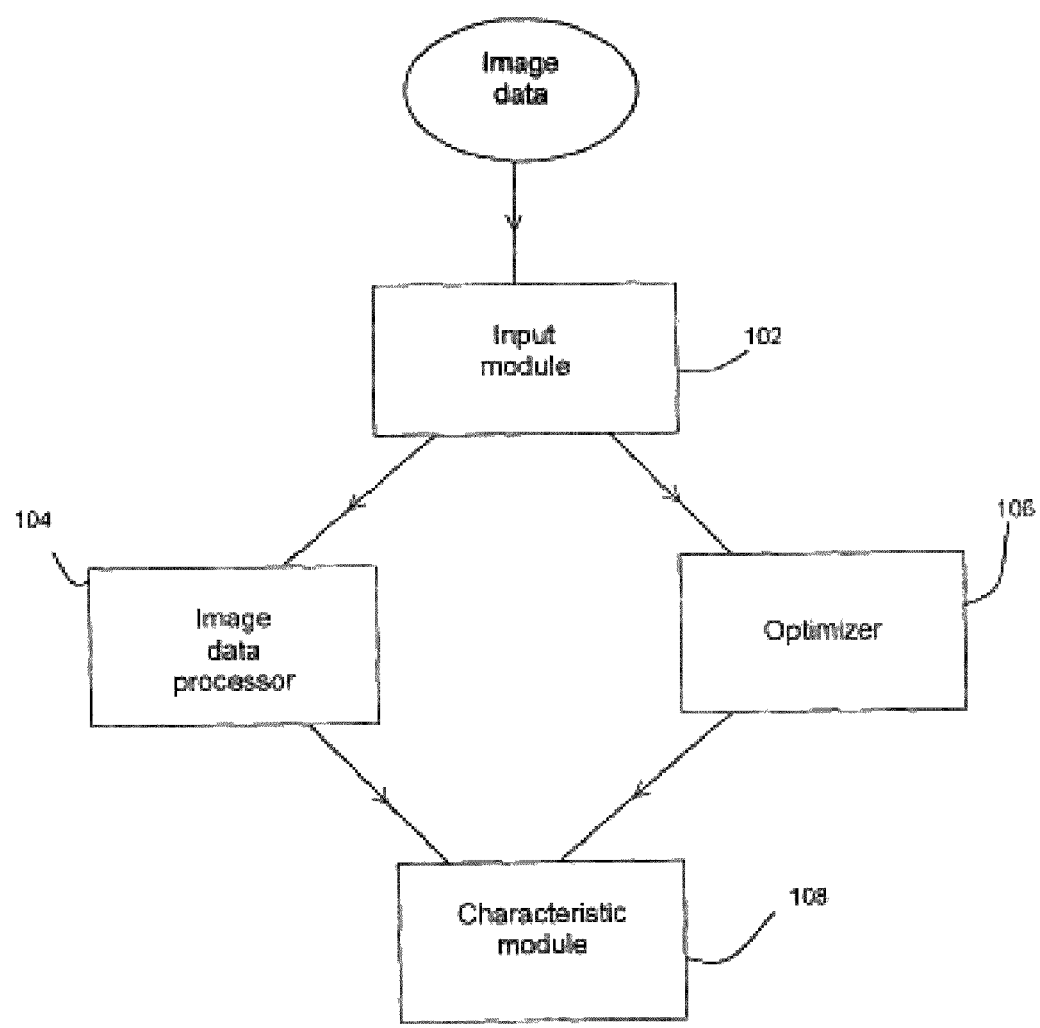
FIG. 6. Block diagram of a system for characterizing a 3D organization of telomeres of samples from subjects having or suspected of having AD.

FIG. 6 shows a block diagram of a system 100 for characterizing a 3D organization of telomeres in samples from subjects having or suspected of having AD. The system 100 includes an input module 102, an image data processor 104, an optimizer 106 and a characteristic module 108.

An input module 102 can be used to input image data of the 3D organization of telomeres. The input module 102 includes appropriate hardware and/or software, such as a CD-ROM and CD-ROM reader, DVD and DVDreader or other data storage and reading means including for example external hard drives. The inputting performed by the input module 102 need not be from outside the system 100 to inside the system 100. Rather, in some embodiments, the inputting of data may describe the transfer of data from a permanent storage medium within the system 100, such as a hard disk of the system 100, to a volatile storage medium of the system 100, such as RAM.

The image data can be obtained using regular or confocal microscopy and can include the intensities of one or more colors at pixels (totaling, for example, 300×300 or 500×500) that comprise an image of a nucleus. The image data can also be grey level image data of a nucleus that has been appropriately stained to highlight telomeres. Several images (on the order of 100) are obtained corresponding to slices along a particular axis. Thus, the image data may correspond to a total of about $2.5 \times 10^7$ pixels. In one embodiment, the slices may be on the order of 100 nanometers apart. In this manner, the image data accounts for the 3D quality of the organization of telomeres. In addition, the confocal microscope is able to obtain the intensity of two colors, for example blue and green, of the nucleus at every pixel imaged, thereby doubling the amount of data points.

To obtain an image of telomeres, a stain such as DAPI (4',6-diamidino-2-phenylindole) can be used to preferentially mark the heterochromatin material that comprises DNA. A second stain, such as cy3, together with an appropriate label, such as PNA telomere probe, can be used to mark the telomeric portion of the heterochromatin material.

To improve the quality of the image data, various techniques can be brought to bear as known to those of ordinary skill, such as constrained iterative deconvolution of the image data to improve resolution. Such constrained iterative deconvolution may not be required if confocal, instead of regular, microscopy is used as the image data may be of superior resolution. In addition, other instruments, such as an apotome, may be used to improve the quality of the image.

In an embodiment, the 3D organization is characterized by specifying at least one of $\bar{d}$ and $\sigma$, where $\bar{d}$ is the average distance of the set of distances, and $\sigma$ is the standard deviation of the set of distances.

In another embodiment, the characterization is used to monitor and/or diagnose Alzheimer's disease by comparing the at least one of $\bar{d}$ and $\sigma$ to a corresponding control value.

In an embodiment, the method of characterizing a 3D organization of telomeres comprises:
(i) inputting image data of the 3D organization of telomeres; and
(ii) using an image data processor for finding a three dimensional geometrical shape that best encompasses the 3D organization, wherein the geometrical shape is an ellipsoid having principal axes $a_1, a_2$, and $a_3$ and wherein said shape is used to characterize the 3D organization.

The image data processor 104 processes the image data to find a set of coordinates $\{(x_i, y_i, z_i)\}$, i=1, ..., N, where $(x_i, y_i, z_i)$ is a position of the ith telomere. For this purpose, the image data processor 104 identifies "blobs" within the image data that can be identified as a telomere using a segmentation process. Each blob identified as a telomere has a non-negligible volume (for example, a small telomere may have a volume of 4×4×4 pixels, a large one a volume of 10×10×10, where the size of the nucleus may be approximately 200×200×100 pixels). There is some freedom, therefore, in choosing "the position" of the telomere. One possibility is to choose for this position the center of gravity of the telomere, or more generally, the telomere organization.

In an embodiment, the ellipsoid is an oblate spheroid with $a_1$ approximately equal to $a_2$.

In an embodiment, an oblateness ratio, $a_3/a_1$ or $a_1/a_3$, is used to characterize the 3D organization.

In an embodiment, the method for characterizing a 3D organization of telomeres comprises:
(i) inputting image data of the 3D organization of telomeres and
(ii) obtaining from the image data using an image data processor at least one of a set of intensities $\{I_i\}$, a set of volumes $\{V_i\}$ and a set of three dimensions $\{(Dx_i, Dy_i, Dz_i)\}$, i=1, ..., N, where $I_i$ is a total or average intensity, $V_i$ is a volume, and $(Dx_i, Dy_i, Dz_i)$ are principle axes of an ellipsoid describing the ith telomere, respectively, wherein the at least one is utilized to characterize the 3D organization.

In an embodiment, said characterization is used to monitor and/or diagnose Alzheimer's disease and/or treatment efficacy by comparing a quantity obtained from at least one to a control value or reference signature.

In an embodiment, the quantity is an average of the members of $\{I_i\}$, $\{V_i\}$ or $(Dx_i, Dy_i, Dz_i)$.

In an embodiment, the method for characterizing a 3D organization of telomeres comprises:
(i) obtaining image data of the 3D organization of telomeres obtained using a microscope;
(ii) inputting the image data of the 3D organization of telomeres obtained using the microscope; and
(iii) finding a parameter of the 3D organization that measures a deviation of the 3D organization from a planar arrangement, the deviation used to characterize the 3D organization.

In yet another embodiment, the method for characterizing a 3D organization of telomeres of sample cells comprises:
(i) obtaining image data of the 3D organization of telomeres obtained using a microscope;
(ii) inputting the image data of the 3D organization of telomeres;
(iii) processing the image data to find a set of coordinates $\{(x_i, y_i, z_i)\}$, i=1, ..., N, where $(x_i, y_i, z_i)$ is a position of the ith telomere;
(iv) finding a plane that is closest to the set of coordinates;
(v) finding a set of distances $\{d_i\}$, i=1, ..., N, where $d_i$ is the distance between $(x_i, y_i, z_i)$ and the plane, wherein the set $\{d_i\}$ is utilized to characterize the 3D organization; and
(vi) visually displaying the 3D organization of the telomeres.

In an embodiment, the method for characterizing a 3D organization of telomeres of sample cells is performed on a system for characterizing a 3D organization of telomeres.

In an embodiment, the system comprises:
(i) an input module for inputting image data of the 3D organization of telomeres;
(ii) an image data processor for processing the image data to find a set of coordinates $\{(x_i, y_i, z_i)\}$, i=1, ..., N, where $(x_i, y_i, z_i)$ is a position of the ith telomere;
(iii) an optimizer for finding a plane that is closest to the set of coordinates; and
(iv) a characteristic module for finding a set of distances $\{d_i\}$, i=1, ..., N, where $d_i$ is the distance between $(x_i, y_i, z_i)$ and the plane, wherein the set $\{d_i\}$ is utilized to characterize the 3D organization.

The optimizer 106 finds a plane $P^{min}$ that is closest to the set of coordinates. To find the closest plane, the distance $D_i$ between the location of the ith telomere, $(x_i, y_i, z_i)$ and the plane given by $ax+by+cz=0$ is considered:

$$D_i = \frac{ax_i + by_i + cz_i}{\sqrt{a^2 + b^2 + c^2}}.$$

The optimizer 106 finds the parameters a, b, c, d that minimize the function $$\sum_{i=1}^{N} D_i(a, b, c, d).$$

The characteristic module 108 proceeds to find at least one parameter that can be used to characterize the 3D organization of telomere". "Parameters used to characterize the organization of telomeres" include:

1) A set of distances $\{d_i\}$, i=1, ..., N, where $d_i$ is the distance between $(x_i, y_i, z_i)$ and the plane $P^{min}$.

2) $\bar{d}$ and $\sigma$, the average distance and standard deviation of the set of distances $\{d_i\}$:

$$\bar{d} = \frac{1}{N}\sum_{i=1}^{N} d_i,$$

and $$\sigma^2 = \sum_{i=1}^{N} \frac{(d_i - \bar{d})^2}{N},$$

respectively.

3) A three dimensional geometrical shape that best encompasses the 3D organization. For example, the geometrical shape can be the ellipsoid, having principal axes $a_1, a_2$, and $a_3$ that best encompasses the 3D organization of the telomeres. Several definitions of "best encompasses" can be used. For example, the ellipsoid that best encompasses the telomeres can be defined as the ellipsoid of smallest volume that encloses a certain fraction (e.g., 100%) of the telomeres. If a set of more than one ellipsoid fulfills this condition, other restrictions can be used to reduce the set to just one ellipsoid, such as further requiring the ellipsoid to have the smallest largest ratio of principle axes (i.e., the "most circle-like" ellipsoid). It should be understood that other definitions of "best encompasses" the telomeres can be used. It has been observed that the ellipsoid that best encompasses the telomeres often approximates an oblate spheroid with $a_1$ approximately equal to $a_2$. In such case, it is sufficient to specify just $a_2$ and $a_3$. Alternatively, an oblateness ratio, $a_3/a_1$ or $a_1/a_3$, can be used to characterize the oblate spheroid describing the organization of the telomeres.

4) A set of volumes $\{V_i\}$, where $V_i$ is the volume of the ith telomere.

5) A set of three dimensions $\{(Dx_i, Dy_i, Dz_i)\}$, i=1, ..., N, where $(Dx_i, Dy_i, Dz_i)$ are principle axes of an ellipsoid describing the ith telomere.

6) A set of intensities $\{I_i\}$, i=1, ..., N, where $I_i$ is the total intensity of the ith telomere. (In other embodiments, instead of the total intensity, the average intensity of each telomere can be computed.) That is, if the ith telomere is associated with K pixels, then $$I_i = \sum_{j=1}^{K} I_{i,j}$$

where $I_{i,j}$ is the intensity of the jth pixel of the ith telomere.

In the last three cases, the sets can be used to calculate statistical measures such as an average, a median or a standard deviation.

The parameters 1-5 outlined above characterize the 3D organization of the telomeres by focusing on the geometrical structure of the telomeres. Parameters 1 and 2 are motivated by the finding that, especially during the late G2 phase of the cell cycle, telomeres tend to lie on a plane. Parameters 1 and 2 measure deviations of telomeres from a planar arrangement.

Parameter 3 attempts to describe, with features, such as the three principal axes of an ellipsoid or the oblateness ratio, the overall shape of the 3D organization. While parameters 1-3 are global geometric characteristics, dealing with the overall shape of the organization, parameters 4 and 5 are local geometric characteristics in the sense that they involve the geometry of each individual telomere.

The final parameter is also local, involving the intensity of each individual telomere.

In an embodiment, the 3D organization is characterized by specifying at least one of $\bar{d}$ and $\sigma$, where $\bar{d}$ is the average distance of the set of distances, and $\sigma$ is the standard deviation of the set of distances.

In an embodiment, the system further comprises a diagnosis module for comparing the at least one of $\bar{d}$ and $\sigma$ to a corresponding standard value to monitor or diagnose Alzheimer's disease.

In another embodiment, the method for characterizing a 3D organization of telomeres in the sample comprises:

(i) inputting image data of the 3D organization of telomeres; and (ii) using an image data processor for finding a parameter of the 3D organization that measures a deviation of the 3D organization from a planar arrangement, the deviation used to characterize the 3D organization.

In an embodiment, a system is used for characterizing a 3D organization of telomeres in the sample, the system comprising (i) an input module for inputting image data of the 3D organization of telomeres;

(ii) an image data processor for processing the image data to find a set of coordinates $\{(x_i, y_i, z_i)\}$, i=1, ..., N, where $(x_i, y_i, z_i)$ is a position of the ith telomere; and (iii) a characteristic module for finding a parameter of the distribution that measures a deviation of the distribution from a planar arrangement, the deviation used to characterize the 3D organization.

In an embodiment, the method for characterizing a 3D organization of telomeres comprises:

(i) obtaining image data of the 3D organization of telomeres obtained using a microscope;

(ii) inputting the image data of the 3D organization of telomeres obtained using the microscope;

(iii) processing the image data to find a set of coordinates $\{(x_i, y_i, z_i)\}$, i=1, ..., N, where $(x_i, y_i, z_i)$ is a position of the ith telomere;

(iv) finding a plane that is closest to the set of coordinates; and (v) finding a set of distances $\{d_i\}$, i=1, ..., N, where $d_i$ is the distance between $(x_i,y_i,z_i)$ and the plane, wherein the set $\{d_i\}$ is utilized to characterize the 3D organization.

In another embodiment, the method of characterizing a 3D organization of telomeres, comprises:

(i) obtaining image data of the 3D organization of telomeres obtained using a microscope;

(ii) inputting the image data of the 3D organization of telomeres obtained using the microscope; and (iii) finding a three dimensional geometrical shape that best encompasses the 3D organization, wherein the geometrical shape is an ellipsoid having principal axes $a_1, a_2$, and $a_3$ and wherein said shape is used to characterize the 3D organization.

In another embodiment, the method for characterizing a 3D organization of telomeres, comprises:

(i) obtaining image data of the 3D organization of telomeres obtained using a microscope;

(ii) inputting the image data of the 3D organization of telomeres obtained using the microscope; and (iii) obtaining from the image data at least one of a set of intensities $\{I_i\}$, a set of volumes $\{V_i\}$ and a set of three dimensions $\{Dx_i,Dy_i,Dz_i\}$, i=1, ..., N, where $I_i$ is a total or average intensity, $V_i$ is a volume, and $(Dx_i,Dy_i,Dz_i)$ are principle axes of an ellipsoid describing the ith telomere, respectively, wherein the at least one is utilized to characterize the 3D organization.

In an embodiment, determining the 3D organization of telomeres and comparing to a control is a computer implemented method.

In an embodiment, the computer implemented method is TeloView In another embodiment, the computer implemented method is an automated method such as TeloScan.

For example, the slides can be analyzed using a SpotScan system (Applied Spectral Imaging, Migdal HaEmek, Israel) and three-dimensional TeloScan software. Teloscan is an automated 3D scaning software that can be used for obtaining telomere signatures in interphase nuclei based on three-dimensional fluorescent in situ hybridization (3D-FISH).

Automated methods for example permit an increased speed of the scan. For example, approximately 10,000-15,000 cells/hour can be scanned by 3D (see for example method described in Example 2). Further the methods have applicability in scenarios where there are very low numbers of cells in the sample.

The data were acquired with a high-throughput scanning/acquisition system that allows to measure cells and acquire 3D images of nuclei at high resolution with 40× or 60× oil and at a speed of 10,000-15,000 cells h(−1), depending on the cell density on the slides. The automated scanning, TeloScan, is suitable for large series of samples and sample sizes. The system in an embodiment uses a fully automated Olympus BX61 microscope (Olympus, Center Valley, Pa.) equipped with filters for DAPI and tetramethyl rhodamine iso-thiocyanate (TRITC); the software included CaseDataManager 6.0 and ScanView (Applied Spectral Imaging, Migdal Ha-Emek, Israel). Imaging can for example be done with a ×60 magnification oil objective. For each cell, images of for example 10 focal planes approximately 0.7 μm apart can be collected. SpotScan can be used to analyze the three-dimensional data based on DAPI (nucleus) and TRITC (telomeres). The data collected from each scan includes for example information on number of signals, signal intensity, and the existence of aggregates within each nucleus examined. Three hundred nuclei per 20 minutes per scanned slide were classified according to their number of telomeres and recorded.

Kits

A further aspect included is a kit for use in a method described herein comprising: a sterile swab for collecting buccal cells; a receptable for receiving the swab labelled with a unique identifier; and instructions of where to send the buccal cell swab sample for analysis.

In another embodiment, the kit comprises one or more of:
a sterile collection swab for collecting a buccal cell sample;
a receptable for receiving the collection swab labelled with a unique identifier; and one or more of:
a microscope slide;
a fixative solution for 3D preservation;
wash solution;
dehydration solution; and
instructions for performing a method described herein.

For example as mentioned below, buccal swabs can be acquired and verified to be of high quality. In an embodiment, swabs are Epicentre Catch-A11 sample collection swabs. In an embodiment, the microscope slide is a VWR pre-cleaned frosted microscope slide. In an embodiment, the fixative solution is 3.7% formaldehyde/1× phosphate buffered saline, and/or the wash solution is 1×PBS In an embodiment, the dehydration solution is ethanol which can for example be diluted to 70%, 90% and 100% ethanol for multiple dehydration steps.

The following non-limiting examples are illustrative of the present disclosure:

EXAMPLES

Example 1

Telomeres are hexanucleotide repeats (TTAGGG) of DNA found at the ends of mammalian chromosomes that are associated with telomere-binding proteins known as shelterins [Watson, 1972; Olovnikov, 1972; de Lange, 2005]. These proteins function as protective caps to prevent chromosomal end-to-end fusions [Kruk et al., 1995]. Telomeres shorten during each successive cell replication due to the end replication problem [Wynford-Thomas et al., 1997], eventually reaching a state of critically short telomere length that normally results in cell senescence [Allsopp et al., 1992; Kipling et al., 1999]. In germ cells, stem cells and some cancer cells, shortened telomeres can be extended by the enzyme telomerase or by activating alternative telomere lengthening mechanisms [Greider et al., 1985; Wojtyla et al., 2011; Muntoni et al., 2005]. Most somatic cells do not, however, express telomerase. The shortening of telomeres during each round of cell division is part of the natural aging of cells [Vaziri et al., 1993]. It has been well documented that telomere shortening and dysfunction are closely related to the pathogenesis of numerous diseases including cancers [Mai, 2010; Charames et al., 2003; Meeker et al., 2004; Rampazzo et al., 2010], cardiovascular diseases [Epel et al., 2008; Balasubramanyam et al., 2007], dyskeratosis congenita [Vulliamy et al., 2004; Bessler et al., 2007; Batista et al., 2011], atherosclerosis [Samani et al., 2001], and dementia [Jenkins et al., 2006; Kume et al., 2012]. Telomere dysfunction is a marker of cellular aging and has been associated with age-related conditions, including Alzheimer's Disease (AD) [Panossian et al., 2003; Jenkins et al., 2008; Maeda et al., 2008].

AD is presently the most common form of dementia, accounting for 50-80% of all cases in Canada and the United States [Alzheimer's Association, 2012; Alzheimer Society of Canada]. It is a neurodegenerative condition clinically characterized by cognitive impairments including memory loss, visual-spatial and language impairments [Frank, 1994; Forstl et al., 1999; Taler et al., 2008]. The risk of developing AD increases significantly in individuals 65 years of age and older, with the prevalence of the disease doubling every 5 years after the age of 65 [Alzheimer's Association, 2012]. It is predicted that AD will affect 1 in 85 individuals globally by 2050 [Brookmeyer et al., 2007; World population prospects]. AD is ultimately fatal, although existing treatment options look to temporarily improve patient symptoms and quality of life [National Institute on Aging; Mölsä et al., 1986; Mölsä et al., 1995].

AD has been associated with genomic instability biomarkers, including aneuploidy of chromosomes 17 and 21 [38-41] and telomere shortening [Samani et al., 2001; Panossian et al., 2003; Jenkins et al., 2008; Thomas et al., 2008; Juan et al., 2012]. Genomic instability may, therefore, play an important role in the pathogenesis of AD.

The primary objective of the study described in this example was to collect and analyze nuclear three-dimensional (3D) telomeric information from buccal cells (BCs) in order to investigate changes in the 3D telomeric architecture of AD patients compared to age (+/−5 years) and sex-matched, cognitively normal controls. This pilot study consisted of 82 participants; forty-one patients with AD were compared to forty-one caregiver controls according to the following 3D parameters: i) telomere length, ii) telomere number, iii) telomere aggregation, iv) nuclear volume, and v) a/c ratio (see "a/c ratio as measured in 3D" in Materials and Methods). A secondary aim of the study was to investigate whether there were differences in the 3D telomeric architecture among the three stages (mild, moderate and severe) of AD using the same five parameters. BCs were used in this study as they are neuro-ectoderm derived cells that can be collected non-invasively [Nazarenko et al., 1999]. Results are reported for five different nuclear 3D telomeric parameters.

Material and Methods:

Clinical and Neuropsychological Characterization of Participants

Diagnosis of AD was made at the Queen's Memory Clinics according to the National Institute of Neurological and Communicative Disorders and Stroke, and the Alzheimer's Disease and Related Disorders Association (NINCDS-ADRDA) criteria [McKhann et al., 1984; Dubois et al., 2007]. Patients were categorized as mild, moderate or severe AD based on their regular clinic visits and their scores on the Montreal Cognitive Assessment (MoCA) and the Mini-Mental State Examination (MMSE) (Table 1) [Nasreddine et al., 1995; Folstein et al., 1975; McDowell et al., 1997]. Patients with a MoCA score of >18/30 and/or MMSE score of 22/30 were considered to have mild AD. Patients with a MoCA score of ≤18/30 and/or MMSE score between 21/30 and 16/30 were considered to be in the moderate stage of AD, whereas patients with an MMSE score lower than 16/30 were considered to have severe AD (Table 1) [Nasreddine et al., 1995; Folstein et al., 1975; McDowell et al., 1997].

All AD patients were on standard AD treatment with cholinesterase inhibitors according to the Canadian guidelines for treatment of dementia [Herrmann et al., 2008; Gauthier et al., 2012]. In total, 41 patients diagnosed with AD were compared to both their own age (+/−5 years) and sex-matched cognitively normal caregiver as well as the entire cohort of cognitively normal caregivers. 21 mild AD patients, 10 moderate AD patients, and 10 severe AD patients were evaluated. The study was approved by the Queen's University Research Ethics Board and all 82 participants provided written informed consent. Caregiver controls were also assessed for overall health prior to participation in the study.

Buccal Cells of Neuro-Ectodermal Origin

Buccal swabs were acquired and verified to be of high quality by the Queen's Memory Clinics' personnel and collaborating physician. Using Epicentre Catch-A11 sample collection swabs, buccal cells were collected in duplicate from each participant and smeared onto microscope VWR pre-cleaned frosted micro slides immediately afterward. Once slides were air-dried, they were frozen at −20° C. until shipped to the Manitoba Institute of Cell Biology on dry ice.

Three-Dimensional Quantitative Fluorescent In Situ Hybridization (3D Q-FISH)

Three-dimensional quantitative fluorescent in situ hybridization (3D Q-FISH) was performed as described previously [Vermolen et al., 2005]. Slides were fixed in fresh 3.7% fornnaldehyde/1×PBS (20 min) and washed in 1×PBS (3×5 min). Slides were then incubated in 0.5% Triton X-100 for 10 min, followed by incubation in 20% glycerol for one hour. Four repeated cycles of a glycerol/liquid nitrogen freeze-thaw treatment were then performed to preserve the 3D nuclear architecture of the cells [Cremer et al., 2008]. Following the freeze-thaw treatment, slides underwent 1×PBS washes (3×5 min) and incubation in 0.1N HCl (5 min). Prior to equilibration in 70% Formamide/2×SSC at pH 7.0, slides were washed twice for 5 min in 1×PBS. After equilibration, 6 µl of telomere PNA probe (DAKO; Glostrup, Denmark) was applied onto the slides and sealed with rubber cement. Using a Hybrite™ (Vysis; Abbott Diagnostics, Des Plains, Ill.), a 3-minute denaturation of the probe and nuclear DNA occurred at 80° C. followed by hybridization for 2 hours at 30° C. Slides then underwent a series of washes in 70% Formamide/10 mM Tris at pH 7.4 (2×15 min), 1×PBS (1 min), 0.1×SSC at 55° C. (5 min), and 2×SSC/0.05% Tween 20 (2×5 min). Subsequently, cells were counterstained with 0.1 µl/ml, 4'6-diamidino-2-phenylindole (DAPI) and any excess DAPI was removed with deionized distilled water. Cells were finally dehydrated in 70%, 90% and 100% ethanol (2 min each), air-dried and mounted in Vectashield (Vector Laboratories, Burlington, Ontario, Canada).

Image Acquisition

Using an Axiolmager Z2 microscope with a cooled AxioCam HR B&W (Carl Zeiss, Toronto, Canada) along with AxioVision 4.8 software (Carl Zeiss), 3D images of buccal cells were acquired. Cyanine 3 (Cy3) and DAPI filters were used with a 63×/1.4 oil objective lens (Carl Zeiss) in multichannel mode in order to visualize the telomere peptide nucleic acid (PNA) probe signals and nuclear DNA staining, respectively. For every fluorochrome, 80 image z-stacks were taken with a sampling distance of 200 nm along the z-axis and 102 nm in the x, y direction. To standardize fluorescent intensity between samples, the same exposure time of 800±50 milliseconds was used for Cy3 imaging of all interphase nuclei. Additionally, tricolor beads (Molecular probes, M7901, Eugene, USA) were used to ensure no variation in light source and imaging conditions occurred (data not shown). Imaging was followed by deconvolution using the constrained iterative algorithm [Schaefer et al., 2001]. Deconvolved images were converted to tagged image file format (TIFF) and exported for 3D quantitative analysis using TeloView software. Thirty interphase nuclei from each AD patient, as well as each healthy control, were analyzed blindly.

Structured Illumination Microscopy

Three-dimensional structured illumination microscopy (3D-SIM) was performed using a Zeiss ELYRA system. The associated image reconstruction was done with ZEN 2012 (Carl Zeiss). A 63×/1.4 NA oil immersion lens was used in combination with a 23 micron grid with 405 nm excitation light and a 420-480 nm emission filter. The reconstruction parameters and z-spacing were all Zeiss' defaults and/or automatic optima.

SIM allows superresolution imaging, i.e. it achieves a resolution beyond the classical diffraction limit by heterodyne detection in epifluorescence microscopy of the sample illuminated with patterned light and subsequent image reconstruction [Gustafsson, 2000].

Image Analysis

Quantification of the nuclear 3D telomeric signals was performed using TeloView, a software program developed in collaboration with the Delft University of Technology in 2005 [Vermolen et al., 2005]. Teloview loads the 3D images and displays a maximum projection along the three cardinal axes, x, y, and z. After segmentation, the 2D display indicates the location of the automatically detected telomere spots for visual verification. The image processing was done with the toolbox DIPImage (http://www.qi.tnw.tudelft.nl/DIPlib/). The version of DIPImage used in this study operates under MatLab (The MathWorks, Natick, Mass., USA).

In this study, Teloview computed five parameters for each sample: i) telomeric signal intensity, ii) number of telomeric signals, iii) number of telomere aggregates, iv) nuclear volume of each cell, v) a/c ratio (see "a/c ratio as measured in 3D" in Materials and Methods). Together, these parameters are termed, "3D telomere profiles". The Manitoba laboratory personnel were blinded to sample diagnoses, which were only revealed upon completion of sample imaging and analysis.

3D Relative Fluorescent Telomere Signal Intensity

It has been shown that the PNA probe hybridizing to the telomeric end is directly proportional to the length of the telomeric DNA; the relative fluorescent telomeric signal intensity thus represents the length of the telomeres in arbitrary units [Poon et al., 1999]. Subsequently, kilo base pairs (kB) were computed from this intensity in order to evaluate telomere length. This was calculated through a conversion factor derived from Raji cells, a Burkitt's lymphoma cell line used as a control. Once Raji cells were harvested, half underwent telomere restriction fragment (TRF) analysis via Southern blot while the rest underwent PNA Q-FISH using identical conditions as set for the AD buccal cells. Using TeloView, an average telomere intensity was calculated for the Raji cells. This correlated with the telomere length resulting from the TRF analysis, thus deriving the conversion factor. The average intensities of AD buccal cells were then converted into kB using this conversion factor.

For this study, short telomeres were defined as signals at a relative fluorescent intensity from 0 to 20,000 arbitrary units. Mid-sized telomeres were considered to be in the relative fluorescent intensity range from 20,001 to 40,000 units, and long telomeres were defined as signals at a relative fluorescent intensity range of above 40,000 units.

Number of Telomere Signals as Measured in 3D

The number of telomeric signals represents the total number of telomeres present in each cell, as measured by TeloView. Although it is expected that 92 telomeres are observed in normal human somatic cells, telomere numbers between 40-64 were considered normal in this study, as previously described [Chuang et al., 2004]. In previous work, approximately 50 separated telomere regions were identified in each human cell. Similar results have also been described by Nagele et al (2001), Weierich et al (2003) and De Vos et al (2008) [Nagele et al., 2001; Weierich et al., 2003; De Vos et al., 2009]. This is most likely due to neighbouring telomeres that were closer to each other than the optical resolution limit of 200 nm could resolve, and therefore could not be differentiated as separate entities [Knecht et al., 2013]. However, this does not affect the 3D analysis of the telomere distribution in the nucleus as long as the hybridization efficiency is high. This was verified by two-dimensional measurements of all the telomeres in metaphase spreads (using the same probe), where at least 90% of the telomeres were unambiguously observed [Chuang et al., 2004; Louis et al., 2005]. Hence, approximately half the number of signals were observed in interphase cells as expected (as verified through metaphase spreads) due to resolution limitations.

Number of Telomere Aggregates as Measured in 3D

Telomere aggregates are defined as clusters of telomeres found in close proximity to each other which cannot be further resolved as separate entities by TeloView at an optical resolution limit of 200 nm (FIG. 1).

3D Nuclear Volume

The nuclear volume of each cell was measured by analyzing the nuclear DAPI stain in the x, y and z dimensions.

a/c Ratio as Measured in 3D

The nuclear space occupied by telomeres can be represented by an ellipsoid with three axes of length a, b and c, where a and b are of equal micron length and c is of a different length, determined by the length in pixels multiplied by the size of each pixel. The micron length and size of each pixel was determined by the physical properties of the camera and microscope. [Vermolen et al., 2005]. The ratio between a and c is called the a/c ratio, and has no unit as it is a dimensionless number. Stages of the cell cycle (G0/G1, S, G2) have characteristic a/c ratios. Thus, by measuring a/c ratio, one can determine exactly where telomeres reside in the cell cycle. It defines progression through cell cycle in interphase cells.

Linear Classification of 3D Parameters

In addition to comparison of the 3D telomere profiles, linear classifiers were used based on the Fisher linear discriminant [Duda et al., 1973] to identify each patient's level of AD severity. The average number and length of telomeres were plotted for each cell and decision lines were drawn in order to classify these measurements as belonging to each of the three AD severity groups utilizing the PR Tools (http://prtools.org/) toolbox for MATlab. The probability of every level of AD severity was normalized to ⅓ each in order to correct for the different number of patients in each group. Each AD case was subsequently judged in terms of whether the result from this classification method corresponded with the biological diagnosis.

Statistical Analysis

For each 3D parameter, by-pair analysis comparing each AD patient to his/her matched control was conducted via chi-square analysis or Wilcoxon rank sum tests. As a group of similar AD severity, the comparisons were done using randomized blocks analysis of variance and Mantel Haenszel stratified analysis, followed by the Breslow-Day test for homogeneity across pairs as well as a log-linear analysis. To compare each AD severity to one another, severity effect with nested randomized block anovas was tested for. Significance level was set at p<0.05.

Figure 2:
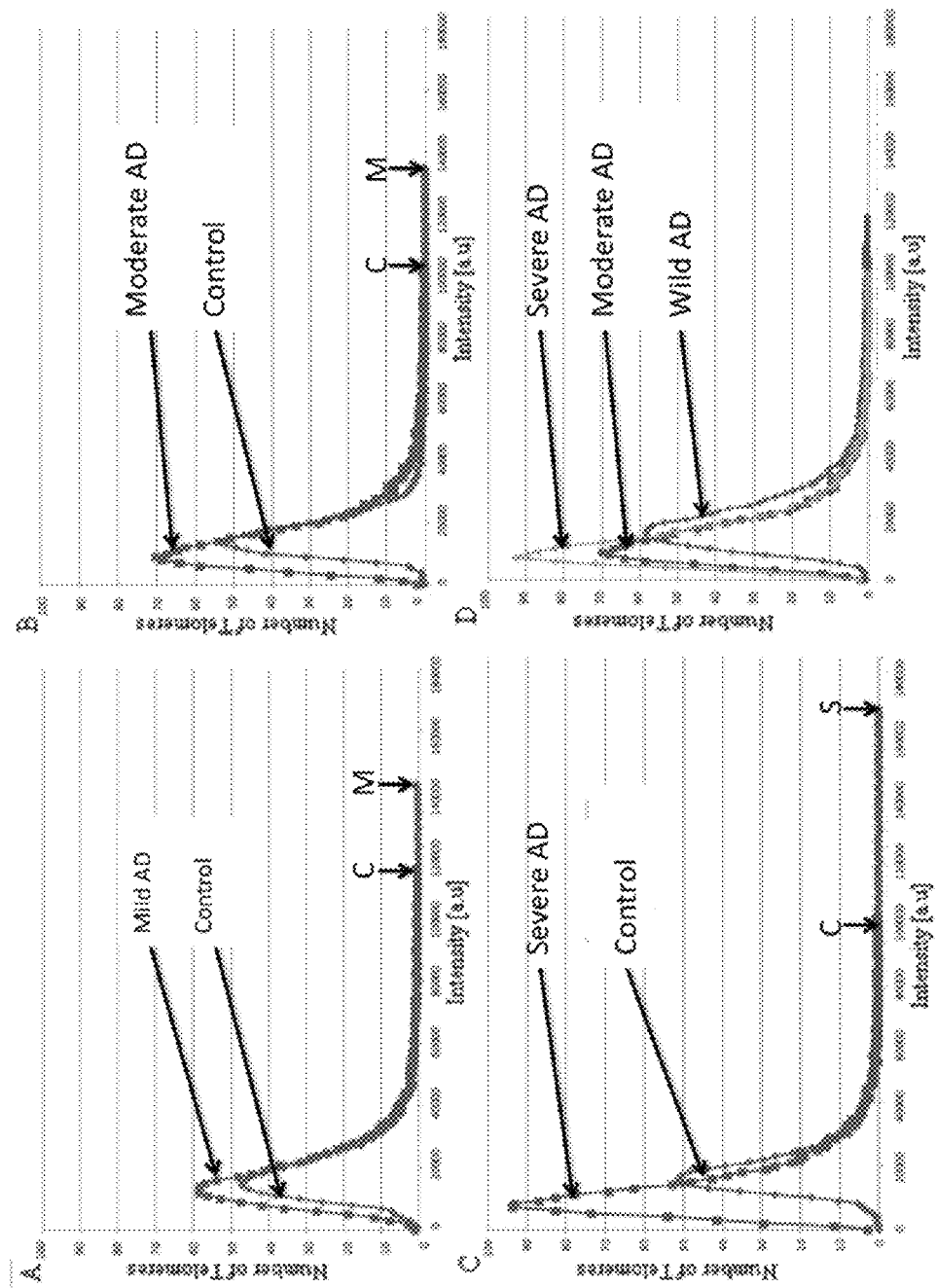
FIG. 2. Average number and length of telomeres in cohorts. The intensity correlates to telomere length in arbitrary units [a.u]. (A) Mild AD patients (squares) compared to their age and sex-matched cognitively normal controls (diamonds). Combined, telomere length and number show a distinct telomeric mild AD profile relative to controls: telomeres are significantly shorter (p=0.005) and slightly increased in mild AD patients (p=0.17) (see Materials and Methods). (B) Moderate AD patients (squares) relative to their age and sex-matched cognitively normal controls (diamonds). Patients have significantly shorter and increased number of telomeres compared to controls (p=0.007; p=0.04, respectively). (C) Severe AD patients (squares) compared to their age and sex-matched cognitively normal controls (diamonds). Patients have significantly shorter and increased number of telomeres compared to controls (p=0.0003; p=0.009, respectively). (D) Comparison of telomere length and number between the three AD severities of mild (diamonds), moderate (squares) and severe (triangles) AD. Compared to mild AD, moderate and severe AD patients have significantly shorter telomeres (p=0.04; p=0.03, respectively). Relative to severe AD, mild and moderate AD patients have significantly fewer telomeres (p=0.004; p=0.01, respectively)

Results 30 interphase nuclei were analyzed from buccal cells of each AD patient (N=41) and matched control (N=41) (Table 1). Using TeloView, AD was studied for the first time from five different nuclear 3D telomeric parameters. The following summarizes the results based on each parameter investigated:

Decreased Telomere Length and Increased Telomere Number in Buccal Cells of AD Patients Compared to Controls, and as AD Progresses FIG. 1 depicts representative 2D and 3D images of telomeres in buccal cells of mild, moderate and severe AD patients relative to controls. An increase in number of telomeres in moderate and severe AD patients was found (p=0.04; p=0.009, respectively). In order to visualize changes in telomere length and number between normal individuals and AD patients, telomere intensity was graphed against the total number of telomeric signals in what was termed, "3D telomeric profiles" (FIG. 2 A-C). As depicted in FIG. 2A, telomeres were significantly shorter in mild AD patients relative to controls (p=0.005). In addition, the total number of telomeres was comparatively increased in mild AD patients, although this value was not significant (p=0.17). Moderate AD patients also showed different 3D telomeric profiles relative to their controls; telomeres were both significantly shorter (p=0.007) and significantly increased in number (p=0.04) (FIG. 2B). Similarly, severe AD patients showed significantly decreased telomere length and increase in telomere number relative to their controls (p=0.0003, p=0.009, respectively) (FIG. 2C).

A comparison among all three stages of AD severity was also done in order to assess whether telomere length and number changed significantly according to the severity of the disease. FIG. 2D is a graphical representation of the results: in terms of telomere number, there was a significant increase between moderate and severe AD patients (p=0.01), where on average, moderate AD patients had 65-85 telomeres and severe AD patients had ≥85 telomeres. Although a trend towards an increase in telomere number between mild and moderate AD patients was detected, this difference was not statistically significant (p=0.86).

In terms of telomere length, there was a distinctly noticeable decrease as AD progressed. The leftward shift of the profiles in FIG. 2D indicates a significant decrease in telomere length between mild and moderate AD patients (p=0.04). This decrease was also seen towards severe AD, but was not significant when comparing moderate and severe AD (p=0.44). Thus, the most significant changes in telomere length occurred between normal and mild, mild and moderate AD (p=0.005; p=0.04, respectively) (FIG. 2D).

In order to discriminate between AD profiles, telomere number were plotted against the length for each of the 41 AD patients. FIG. 3 describes the ranges where the majority of telomeric signals were detected. Subsequently, the space was divided into three parts corresponding to each of the levels of AD severity. This classification had a 9.8% error rate after normalization to equal probability of each AD stage. The exact number of errors is shown in the confusion matrix in Table 2.

Overall, these results show a decrease in telomere length and increase in telomere number between AD patients and controls, and across all levels of AD severity. Changes in telomere intensity in patient groups correlated to a 270, 1480, and 2340 base pair difference between normal and mild, normal and moderate, and normal and severe AD individuals, respectively.

Increase in Telomere Aggregation in Moderate and Severe AD Patients Compared to Controls, and as AD Progresses Telomere aggregation was measured by TeloView (see Materials and Methods) to investigate whether changes in aggregation occurred between AD patients and their controls, as well as among the three AD severities. Results showed a significant increase in telomere aggregation between moderate AD patients and controls (p=0.04) as well as severe AD patients and controls (p=0.01) (Table 3).

Furthermore, a significant increase was seen in telomere aggregation as AD progressed along the three severities (FIG. 1); compared to mild AD patients, there was a significant increase in aggregation in moderate AD patients (p=0.03), and compared to moderate AD patients, there was an increase in telomere aggregation in severe AD patients (p=0.02).

No Significant Alteration in Nuclear Volume of AD Patients Compared to Controls, or Between AD Severities.

Table 3 illustrates the average nuclear volumes of each AD severity and their respective controls. Although results show an overall increase in the nuclear volumes of AD patients, these results were not significant (p>0.05). There was also no trend towards increased nuclear volumes among mild, moderate and severe AD patients (p>0.05).

No Significant Alterations in a/c Ratio of AD Patients Compared to Controls, or Between AD Severities.

In addition to the other 3D parameters, TeloView calculated a/c ratios (see Materials and Methods). Similar to nuclear volume, changes in a/c ratios were not significant across all AD populations and in comparison to matched controls (p>0.05) (Table 3).

DISCUSSION

The study described in this example reveals changes in the nuclear 3D telomeric architecture of buccal cells in Alzheimer patients for the first time. Using TeloView, the differences between AD patients and their cognitively normal caregivers were quantified based on five 3D parameters. In addition, this study went one step further by analyzing differences in 3D telomeric architecture among the three disease stages of mild, moderate and severe AD.

The 3D approach to studying structural and nuclear architectural changes in different diseases is an emerging field that has proven to be innovative and successful in many research areas. In particular, the use of 3D telomere profiles in identifying patient populations and subpopulations has been shown to be an accurate and effective method for classifying patient samples, as cells are analyzed individually by TeloView. Changes in the 3D nuclear architecture of cells have been described for numerous diseases, including various carcinomas such as Hodgkin's lymphoma [Guffei et al., 2010], circulating tumor cells [Adebayo et al., 2013], myelodysplastic syndrome and acute myeloid leukemia [Gadji et al., 2012]. It has also been described in different non-cancers including non-age and age-related conditions such as Preeclampsia [Sukenik-Halevy et al., 2009], intrauterine growth restriction placentas [Biron-Shental et al., 2010], Trisomy 21 [Hadi et al., 2009], Hutchinson-Gilford progeria syndrome (HGPS), Werner's syndrome and other lamin A-related conditions [Mounkes et al., 2004; Righolt et al., 2011; Raz et al., 2008], and as shown in this study, in AD.

In this example, it is shown that telomere length and number describe the progression of AD from mild to severe and that each patient can be classified from these measurements (FIG. 3). Most errors occurred close to the decision boundaries; only one outlier—a mild case in the middle of the moderate region—was found (FIG. 3; Table 2). The analysis in FIG. 3 and Table 2 also corresponds with the results from the telomere profile analysiswhich indicate that AD begins with a decrease in telomere length, which is followed by an increase in telomere number later in AD progression.

Although the association between telomere shortening and AD has been documented before [Jenkins et al., 2006; Panossian et al., 2003; Jenkins et al., 2008; Juan et al., 2012], it was not until recently that such a correlation was demonstrated in buccal cells of AD patients and age-matched controls [Thomas et al., 2008]. The results described herein support these findings, showing significantly shorter telomere length in all AD severities relative to their controls ($p<0.05$) (FIG. 2 A-C). Furthermore, comparison among the three levels of AD severity revealed a decreasing trend in telomere length as AD progressed from the mild to severe state. In particular, a significant reduction in telomere length was detected comparing moderate AD profiles to mild AD profiles ($p=0.04$) (FIG. 2D).

This reduction may be due to enhanced cell proliferation during this period, causing telomeres to shorten considerably. Also, telomere length maintenance depends heavily on the telomere binding proteins of the shelterin complex, of which Telomere Repeat Binding Factors 1 and 2 (TRF1, TRF2) are critical members [de Lange, 2005]. A recent study has demonstrated that removal of the entire shelterin complex from mouse telomeres through conditional deletion of TRF1 and TRF2 induced two DNA damage response pathways not previously observed upon deletion of individual shelterin proteins [Sfeir et al., 2012]. Thus, the progressive shortening of telomeres in AD individuals may be attributed to dysfunction of these damage repair pathways. Further research on the roles of shelterin proteins is, therefore, warranted to fully understand telomere length regulation in AD.

The goal of the pilot study described herein was to document whether changes in telomere architecture, including telomere length, occurred in AD patients when compared to caregiver controls. Relative to caregivers, a 270, 1480, and 2340 base pair difference was identified in mild, moderate and severe AD patients, respectively. Similarly, a recent study done by Jacobs et al (2013) compared telomere length of those with APOE-e4 to healthy (non-caregiver) controls and determined that APOE-e4 carriers, on average, had increased pre-disposition to developing AD [Jacobs et al., 2013]. Telomere length of APOE-e4 carriers was found to be approximately 400 bp shorter relative to healthy controls.

As stress on caregivers has been shown to cause accelerated telomere shortening [Epel et al., 2004], the use of caregiver controls in this study may be considered a limitation. However, as results presented in this example showed significant changes in AD patients relative to caregivers, an even greater margin of difference is expected with non-caregiver controls and these results most likely underestimate the true difference.

Using TeloView, an investigation were carried out to determine whether changes in the number of telomeres occurred in AD patients relative to controls. Overall, AD patients showed increased telomeric signals than their normal counterparts. In particular, moderate and severe AD patients showed significantly more telomere numbers than controls ($p=0.04$; $p=0.009$, respectively). Although the cause is yet unknown, the increase in telomere number may partially be attributed to 3D nuclear reorganization of the cells. Using 3D structured illumination microscopy (3D-SIM) (see Materials and Methods), severe AD patients were compared with matched healthy controls to distinguish whether nuclear reorganization occurred in AD patients. FIG. 5 illustrates representative cells from normal and severe AD patients. Morphological changes were evident in AD patients relative to controls, suggesting that chromatin reorganization may play a role in the progression of the disease. Nuclear reorganization has previously been described in Hodgkin's Lymphoma, showing looser chromatin organization and thus a higher display of telomere signals [Duda et al., 1973]. A similar increase—albeit through different mechanisms—may also occur in buccal cells of AD patients.

Furthermore, aneuploidy of chromosomes 17 and 21, well-documented pathological features of AD [Migliore et al., 1997; Migliore et al., 1999; Geller et al., 1999; Thomas et al., 2008], may also contribute to the increase in numbers of telomeres detected in AD.

The increase seen is larger than would could be accounted for with an an extra copy of chr 21 or 17.

In contrast to the findings described herein, a recent study by Jenkins et al (2008) showed a decrease in telomere number in cohorts with dementia or mild cognitive impairment (MCI) compared to patients without dementia or MCI [Jenkins et al., 2008]. As these results were based on T-lymphocytes from whole blood culture of patients, the variability in results may be due to the cell or tissue type used. Furthermore, the cohort size may also be a differentiating factor as the authors of this study used 26 cases in total. In the present example, neuro-ectodermal derived cells from buccal swabs were chosen in order to get more representative results, along with a cohort size of 82 patients.

Among the levels of AD severity, a significant increase in telomere number was observed in severe AD patients from moderate AD patients ($p=0.01$) (FIG. 2D), suggesting that in terms of telomere number, moderate AD patients experience substantial changes and chromosomal instability as they progress to severe AD. In contrast, the difference in telomere number between normal and mild, mild and moderate AD, show only slight increases in telomere number, suggesting that AD patients undergo a more gradual change as they progress from normal to moderate AD.

The third parameter calculated by TeloView referred to the presence of, and changes in, telomere aggregation in AD patients. Telomere aggregates (TAs) are defined as telomeres in close proximity to one another that cannot be resolved as two separate entities at the optical resolution limit of 200 nm [Vermolen et al., 2005]. Previous studies investigating the 3D nuclear organization in normal mammalian nuclei have shown that telomeres in normal cells have a dynamic cell-cycle and tissue-dependent organization [Chuang et al., 2004; Weierich et al., 2003]. They are widely distributed throughout the entire nuclear space and do not overlap one another [Mai et al., 2006]. TAs are therefore abnormalities that occur due to genomic instability in the cell. They are a common feature of telomeric dysfunction in tumors due to their role in initiating breakage bridge fusion (BBF) cycles in cells [Mai et al., 2006]. Once BBF cycles result, the genetic information of the chromosomes becomes remodelled. The formation of TAs is, however, independent of telomere length and telomerase activity [Mai et al., 2006].

Although TA's have been identified to play a key role in genomic instability of tumorigenesis, there have been studies linking the presence of TA's in non-cancers as well, two of which are trisomy 21 and aneuploidy of chromosome 17 [Geller et al., 1999; Thomas et al., 2008 et al., 2009]. A connection between AD and trisomy 21 (Down syndrome) has been indicated by the fact that Down syndrome individuals develop AD neuropathology by the 4th decade of life [Geller et al., 1999]. FIG. 1 displays representative 2D and 3D images of normal, mild, moderate and severe AD individuals from TeloView. As marked by arrows in the 3D depictions, telomere aggregates were visible in all three levels of AD severity. The previously mentioned increase in telomere aggregation of moderate and severe AD patients is visible (p=0.04; p=0.01, respectively) (FIG. 1), suggesting an increase in genomic instability in these patients.

Interestingly, analysis of TAs across all three stages of AD severity revealed a significant increase in aggregation from mild to moderate AD (p=0.03) and moderate to severe AD (p=0.02) (FIG. 1). Successive cell replication with TAs may lead to increased genomic instability resulting in accelerated cell senescence in AD. To our knowledge, TAs have not been studied in AD before.

In addition to telomere length, number and aggregation, TeloView measured the nuclear volume and a/c ratio for each patient. Results showed no significant changes in both the nuclear volume and a/c ratio of AD patients relative to controls, as well as among all three AD severities (p>0.05) (Table 3). This indicates that as AD patients progress between the disease stages, their buccal cells maintain their volume. Since no alterations in a/c ratio were found, it can be seen that at the point of measurement, any minimal changes in nuclear volume that did occur were not related to cell cycle [Echave et al., 2007]. In contrast to the present findings, a study done by Riudavets et al (2007) showed a significant decrease in nuclear volume in AD patients [Riudavets et al., 2007]. However, the authors investigated neurons from the anterior cingulate gyrus (ACG) and CA1 hippocampal region of the brain. Thus, the difference in cell type may account for this variability in results. Furthermore, the study included only 8 patients with symptomatic AD, which may indicate a need for verification of their results with larger cohorts.

Figure 4:
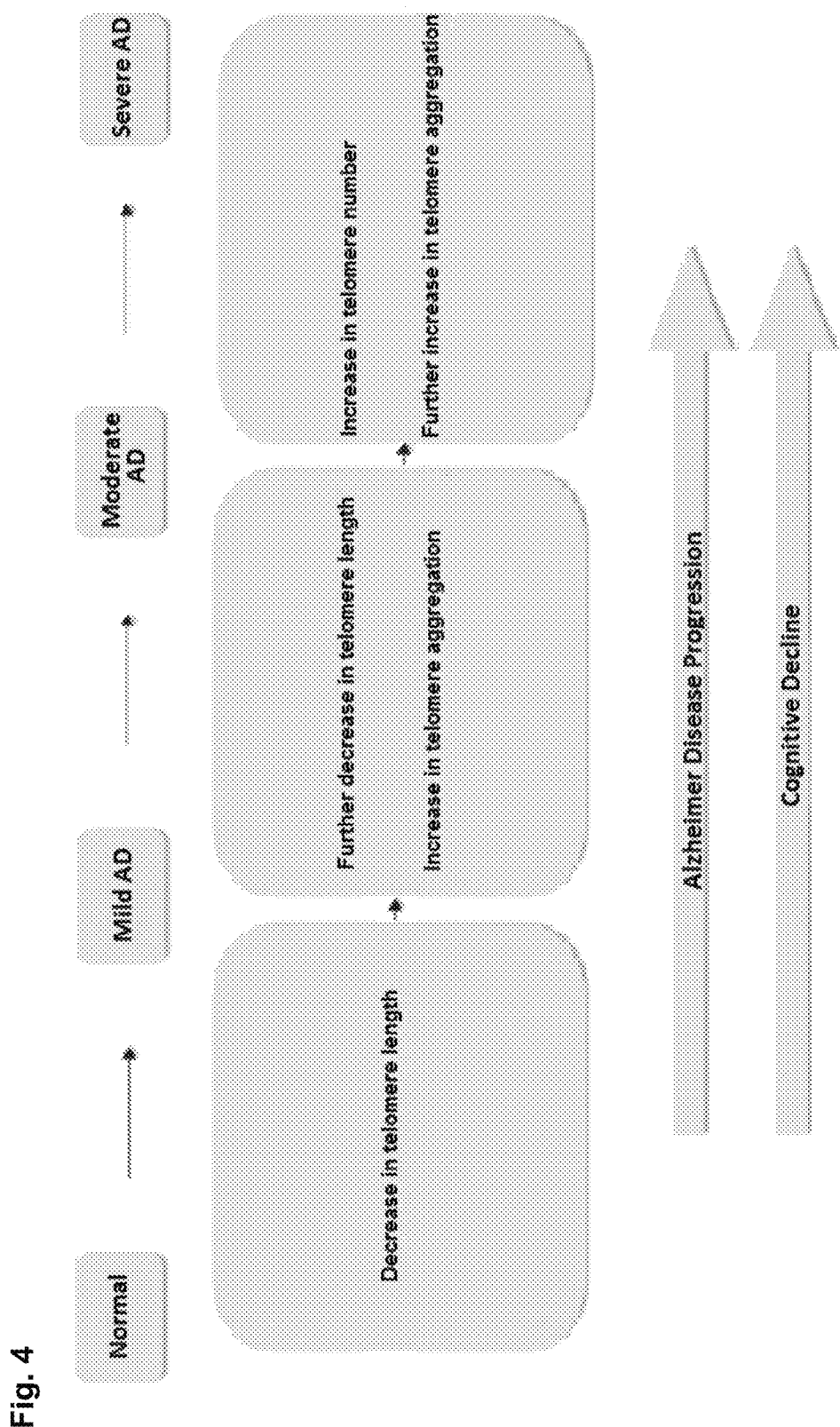
FIG. 4. Progressive changes in nuclear 3D telomeric architecture in buccal cells among AD severities. Results are based on nested randomized block anovas testing of 30 interphase nuclei from each Alzheimer patient and control (see Materials and Methods). Telomere intensity correlates to length and p<0.05 was considered statistically significant. As AD progressed through each stage, significant decreases in telomere length were found between normal individuals and mild AD patients (p=0.005), and between mild and moderate AD patients (p=0.04). A significant increase in the number of telomeres was found as AD progressed from moderate to severe AD stage (p=0.01). Finally, increases in telomere aggregation were found to be significant as AD progressed from mild to moderate AD stage (p=0.03), and moderate to severe AD stage (p=0.02). There were no changes among severities for nuclear volume and a/c ratio (p>0.05).

The progression of nuclear 3D telomeric architectural changes in AD illustrates an increasing trend in telomere number and aggregation concomitant to a decreasing trend in telomere length (FIG. 4). Overall, the present example describes distinct telomeric profiles in mild, moderate and severe AD relative to normal individuals.

Advances in technology describing the 3D nuclear architecture of cells have provided innovative and accurate imaging and quantification methods to study different diseases. The present study used five different 3D parameters to investigate changes in the 3D telomeric architecture of buccal cells in AD patients compared to age and sex-matched cognitively normal caregivers. Furthermore, the study investigated whether these changes occurred among the three levels of AD severity. Significant changes were found in telomere length, number and aggregation, and for the first time 3D methods were described that differentiate between normal, mild, moderate and severe AD individuals. The ability to differentiate normal, mild and moderate AD profiles could have great clinical significance as it allows for early detection of AD, potentially leading to more accurate and individualized treatment for patients. Moreover, the use of buccal cells is ideal, as it is a non-invasive and cost-effective method that is neurologically representative.

TABLE 1

Participant demographics

| Population | Test Score Ranges (MoCA/30:MMSE/30) | Number of subjects | Mean age (years ± S.D) | Gender (Male/Female) |
|---|---|---|---|---|
| Mild AD | >18:≥22 | 21 | 74.5 ± 8.8 | 10/11 |
| Controls, Mild AD | N/A | 21 | 73.7 ± 9.3 | 10/11 |
| Moderate AD | ≤18:21-16 | 10 | 78.8 ± 6.4 | 5/5 |
| Controls, Moderate AD | N/A | 10 | 76.3 ± 6.3 | 5/5 |
| Severe AD | —:<16 | 10 | 74.2 ± 13.0 | 4/6 |
| Controls, Severe AD | N/A | 10 | 73.0 ± 12.9 | 4/6 |

AD = Alzheimer's Disease,
MoCA = Montreal Cognitive Assessment,
MMSE = Mini-Mental State Examination.
All patients were on treatment with cholinesterase inhibitors.

TABLE 2

Confusion matrix for the classification of AD in FIG. 3

| | | Biological Diagnosis | | |
|---|---|---|---|---|
| | | Mild AD | Moderate AD | Severe AD |
| Statistical Classification | Mild AD | 19 | 1 | 0 |
| | Moderate AD | 2 | 8 | 0 |
| | Severe AD | 0 | 1 | 10 |

Confusion matrix illustrating the number of correctly and misclassified AD patients based on their telomere profiles. The weighted error rate is 9.8% based on equal probability of each stage. Of 41 AD patients, two mild AD patients were misclassified as moderate AD, whereas 2 moderate AD patients were misclassified: 1 as mild AD and other as severe AD. Finally, no severe AD patients were incorrectly classified.

TABLE 3

Quantitative summary of nuclear 3D telomeric parameters according to clinical diagnosis

| | | | Nuclear 3D TeleView Parameters | | | | |
|---|---|---|---|---|---|---|---|
| Population | Diagnosis | Number of subjects | Telomere Length (kB) (mean ± S.D.) | Number of telomeres (mean ± S.D.) | Nuclear Volume ($\mu m^2$) (mean ± S.D.) | a/c Ratio (mean ± S.D.) | Telomere Aggregates (mean ± S.D.) |
| Mild AD | Mild AD | 21 | 7.24 ± 1.30 | 34.13 ± 11.99 | 1759 ± 815 | 6.44 ± 2.81 | 3.52 ± 2.36 |
| | Control | 21 | 7.51 ± 1.14 | 33.61 ± 10.78 | 1627 ± 874 | 6.75 ± 3.72 | 3.49 ± 2.10 |
| | | | p = 0.005 | p = 0.17 | p = 0.45 | p = 0.51 | p = 0.12 |

TABLE 3-continued

Quantitative summary of nuclear 3D telomeric parameters according to clinical diagnosis

| Population | Diagnosis | Number of subjects | Nuclear 3D TeleView Parameters | | | | |
|---|---|---|---|---|---|---|---|
| | | | Telomere Length (kB) (mean ± S.D.) | Number of telomeres (mean ± S.D.) | Nuclear Volume ($\mu m^2$) (mean ± S.D.) | a/c Ratio (mean ± S.D.) | Telomere Aggregates (mean ± S.D.) |
| Moderate AD | Moderate AD | 10 | 5.96 ± 1.08 | 36.54 ± 12.64 | 1866 ± 1011 | 6.68 ± 1.49 | 3.94 ± 2.46 |
| | Control | 10 | 7.44 ± 1.62 | 32.60 ± 10.59 | 1495 ± 869 | 6.15 ± 3.62 | 3.30 ± 1.96 |
| | | | p = 0.007 | p = 0.04 | p = 0.15 | p = 0.38 | p = 0.04 |
| Severe AD | Severe AD | 10 | 5.48 ± 1.07 | 43.37 ± 12.26 | 1317 ± 566 | 5.68 ± 2.18 | 4.56 ± 2.54 |
| | Control | 10 | 7.82 ± 1.64 | 32.20 ± 10.43 | 1681 ± 855 | 6.79 ± 4.19 | 3.42 ± 2.12 |
| | | | p = 0.0003 | p = 0.009 | p = 0.21 | p = 0.11 | p = 0.01 |

Summary of nuclear three-dimensional (3D) telomeric parameters of Alzheimer patients and their cognitively normal age (±5 years) and sex-matched controls. Results were based on 3D quantitative analysis of 30 interphase nuclei of buccal cells from each Alzheimer patient and control. There were no significant changes in nuclear volume and a/c ratio across populations (p>0.05). Significant increase in telomere aggregation is shown between moderate and severe AD patients relative to their controls. Abbreviations: AD—Alzheimer's Disease.

Example 2

TeloScan can be used to automate obtaining telomeric organization signatures.

Cell Fixation

Cells are fixed in a way that preserves the shape of 3D nuclei using the following protocol: ~10 million cells were washed in PBS then centrifuged at 120 g for 5 min at room temperature (RT). Cell pellets were resuspended in 5 ml of 75 mM KCl for 10 min at room temperature. After adding 1 ml fixative (3:1; methanol/acetic acid) the tubes were carefully inverted three to four times to gently mix the cells with the fixative. Cells were centrifuged again at room temperature for 10 min at 120 g. The cell pellet was washed with 3 ml fixative and centrifuged for 10 min at 120 g. The final cell pellet was resuspended in 1 ml fixative and stored at −20° C.

Telomere Q-FISH

Telomeres were hybridized with Cy3-labelled peptide nucleic acid probes (DAKO, Denmark) according to our published protocols (Mai 2002). The 3D-fixed cells were washed in freshly prepared methanol/acetic acid (3:1) fixative and positioned on the slides. After air-drying the slides, the cells were fixed in 3.7% formaldehyde/phosphate-buffered saline (PBS) for 20 min, washed three times for 5 min in PBS. After an incubating in TPBS (0.5%, Triton X-100 in PBS) for 10 min the slides were incubated in 20% glycerol for 1 h followed by four freeze-thaw cycles in liquid nitrogen and three washes with PBS. After a 5-min incubation in 0.1N HCl the slides were washed for 5 min in PBS, twice. Prior to the hybridization the samples were equilibrated for 1 h in 70% formamide (Fluka-Sigma Aldrich, St Louis, Mo.), 2×SSC at room temperature. The slides were hybridized with $Cy^3$-labeled telomere-specific PNA probe (DAKO) and washed as previously published (34-36).

DAPI (4',6-diamidino-2-phenylindole) was purchased from Sigma Aldrich (Oakville, ON) and used at 0.1 μg ml$^{-1}$ to counterstain the nuclei on the slides (Louise 2005, Chuang 2004). For the mounting medium we used ProLong® antifade Gold mounting medium (Molecular Probes™, Invitrogen detection technologies, Carlsbad, Calif.). The slides were allowed to dry over night at 4° C. under light protected conditions. The slides were stored at −20° C. until use.

Automated Image Acquisition and Processing

The automated Image acquisition of interphase nuclei was performed using the ScanView system [Applied Spectral Imaging (ASI)], using an Olympus BX61 microscope with a VDS CCD camera, model 1300DS. For scanning purposes the microscope was equipped with a motorized eight-slide stage (Marzhauser, Germany). The 3D-images were acquired with dry 403 objective and a 0.633 c-mount (Olympus) taking 11 focal planes per cell. The axial sampling distance between planes, $\Delta z$, was 500 nm. Exposure times were constant at 200 ms (DAPI) and 1,000 ms ($Cy^3$) throughout the experiments. The tissue sample mode with aggregate detection level of 15 was used to enable segmentation of touching cells and optimized aggregate detection. Cells with <21 detected signal were excluded as nonclassified (NC). Approximately 10,000 to 15,000 cells were scanned and analyzed within 60 min. For analyzing the data, the following software modules of the ScanView system (ASI) were used: SpotScan with TeloScan for the detection of nuclei, signals, and aggregates. Such a large size of data must be managed correctly, and it was performed by the ScanView database module—case data manager (CDM). Up to 30,000 classified single cells per mixture were analyzed.

3D Image Analysis for Telomeres

Telomere measurements were performed using TeloView for the manual 3D-acquisition (Chuang 2004, Vermolen 2005), TeloScan for the automated 3D-acquisition (Gadji 2010). The integrated intensity of each telomere was calculated based on the linear correlation between telomere length and signal intensity.

Telomeric Aggregates

Telomeric aggregates are defined as clusters of telomeres that cannot be resolved as separate signals at the optical resolution limit of 200 nm (63× oil) and 350 nm (40×) (18,35,39).

Statistical Analysis

The statistical significance of the differences was determined using the ANOVA test.

While the present disclosure has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

CITATIONS

Blackburn, E. H. (1991) *Nature* 350, 569-573
Greider, C. W. (1996) *Annu Rev Biochem* 65, 337-365
Blackburn, E. H. (1992) *Annu Rev Biochem* 61, 113-129
Buchkovich, K. J., and Greider, C. W. (1996) *Mol Biol Cell* 7, 1443-1454
Slagboom, P. E., Droog, S., and Boomsma, D. I. (1994) *Am J Hum Genet* 55, 876-882
Rudolph, K. L., Chang, S., Lee, H. W., Blasco, M., Gottlieb, G. J., Greider, C., and DePinho, R. A. (1999) *Cell* 96, 701-712
Chan, S. W., and Blackburn, E. H. (2002) *Oncogene* 21, 553-563
Fry, M., and Loeb, L. A. (1999) *J Biol Chem* 274, 12797-12802
Shen, J. C., Gray, M. D., Oshima, J., Kamath-Loeb, A. S., Fry, M., and Loeb, L. A. (1998) *J Biol Chem* 273, 34139-34144
Yu, C. E., Oshima, J., Fu, Y. H., Wijsman, E. M., Hisama, F., Alisch, R., Matthews, S., Nakura, J., Miki, T., Ouais, S., Martin, G. M., Mulligan, J., and Schellenberg, G. D. (1996) *Science* 272, 258-262
Hayflick, L. (1977) *Handbook of the bilology aging*, 20
Sohal, R. S., and Allen, R. G. (1985) *Basic Life Sci* 35, 75-104
Vulliamy, T. J., Knight, S. W., Mason, P. J., and Dokal, I. (2001) *Blood Cells Mol Dis* 27, 353-357
Charames, G. S., and Bapat, B. (2003) *Curr Mol Med* 3, 589-596
Holland, A. J., and Cleveland, D. W. (2009) *Nat Rev Mol Cell Biol* 10, 478-487
Knecht, H., Bruderlein, S., Wegener, S., Lichtensztejn, D., Lichtensztejn, Z., Lemieux, B., Moller, P., and Mai, S. *BMC Cell Biol* 11, 99
Lothe, R. A., Peltomaki, P., Meling, G. I., Aaltonen, L. A., Nystrom-Lahti, M., Pylkkanen, L., Heimdal, K., Andersen, T. I., Moller, P., Rognum, T. O., and et al. (1993) *Cancer Res* 53, 5849-5852
Colleu-Durel S, G. N., Nourgalieva K, Leveque J, Danic B, Chenal C. (2001) *Oncol Rep* 8, 4
Guffei, A., Sarkar, R., Klewes, L., Righolt, C., Knecht, H., and Mai, S. *Haematologica* 95, 2038-2046
de Lange, T. (2002) *Oncogene* 21, 532-540
Masutomi, K., Yu, E. Y., Khurts, S., Ben-Porath, I., Currier, J. L., Metz, G. B., Brooks, M. W., Kaneko, S., Murakami, S., DeCaprio, J. A., Weinberg, R. A., Stewart, S. A., and Hahn, W. C. (2003) *Cell* 114, 241-253
Harley, C. B., Futcher, A. B., and Greider, C. W. (1990) *Nature* 345, 458-460
Huffman, K. E., Levene, S. D., Tesmer, V. M., Shay, J. W., and Wright, W. E. (2000) *J Biol Chem* 275, 19719-19722
Kirwan, M., and Dokal, I. (2009) *Biochim Biophys Acta* 1792, 371-379
Chang, S., Multani, A. S., Cabrera, N. G., Naylor, M. L., Laud, P., Lombard, D., Pathak, S., Guarente, L., and DePinho, R. A. (2004) *Nat Genet* 36, 877-882
Thomas, P., N J, O. C., and Fenech, M. (2008) *Mech Ageing Dev* 129, 183-190
Thomas, P., Hecker, J., Faunt, J., and Fenech, M. (2007) *Mutagenesis* 22, 371-379
Panossian, L. A., Porter, V. R., Valenzuela, H. F., Zhu, X., Reback, E., Masterman, D., Cummings, J. L., and Effros, R. B. (2003) *Neurobiol Aging* 24, 77-84
Burns, A., Byrne, E. J., and Maurer, K. (2002) *Lancet* 360, 163-165
Du, A. T., Schuff, N., Amend, D., Laakso, M. P., Hsu, Y. Y., Jagust, W. J., Yaffe, K., Kramer, J. H., Reed, B., Norman, D., Chui, H. C., and Weiner, M. W. (2001) *J Neurol Neurosurg Psychiatry* 71, 441-447
Haroutunian, V., Perl, D. P., Purohit, D. P., Marin, D., Khan, K., Lantz, M., Davis, K. L., and Mohs, R. C. (1998) *Arch Neurol* 55, 1185-1191
Kawas, C. H. (2003) *N Engl J Med* 349, 1056-1063
Mattson, M. P. (2004) *Nature* 430, 631-639
Iqbal, K., Grundke-Iqbal, I., Smith, A. J., George, L., Tung, Y. C., and Zaidi, T. (1989) *Proc Natl Acad Sci USA* 86, 5646-5650
Hunt, A. J., and McIntosh, J. R. (1998) *Mol Biot Cell* 9, 2857-2871
Iqbal, K., Alonso, A. C., Gong, C. X., Khatoon, S., Pei, J. J., Wang, J. Z., and Grundke-Iqbal, I. (1998) *J Neural Transm Suppl* 53, 169-180
Petkova, A. T., Ishii, Y., Balbach, J. J., Antzutkin, O. N., Leapman, R. D., Delaglio, F., and Tycko, R. (2002) *Proc Natl Acad Sci USA* 99, 16742-16747
Antzutkin, O. N., Leapman, R. D., Balbach, J. J., and Tycko, R. (2002) *Biochemistry* 41, 15436-15450
Thomas, P., and Fenech, M. (2008) *Mutagenesis* 23, 57-65
Nasreddine, Z. S., Phillips, N. A., Bedirian, V., Charbonneau, S., Whitehead, V., Collin, I., Cummings, J. L., and Chertkow, H. (2005) *J Am Geriatr Soc* 53, 695-699
Folstein, M. F., Folstein, S. E., and McHugh, P. R. (1975) *J Psychiatr Res* 12, 189-198
McKhann, G., Drachman, D., Folstein, M., Katzman, R., Price, D., and Stadlan, E. M. (1984) *Neurology* 34, 939-944
Patterson, C. J., Gauthier, S., Bergman, H., Cohen, C. A., Feightner, J. W., Feldman, H., and Hogan, D. B. (1999) *CMAJ* 160, 1738-1742
Chuang, T. C., Moshir, S., Garini, Y., Chuang, A. Y., Young, I. T., Vermolen, B., van den Doel, R., Mougey, V., Perrin, M., Braun, M., Kerr, P. D., Fest, T., Boukamp, P., and Mai, S. (2004) *BMC Biol* 2, 12
Louis, S. F., Vermolen, B. J., Garini, Y., Young, I. T., Guffei, A., Lichtensztejn, Z., Kuttler, F., Chuang, T. C., Moshir, S., Mougey, V., Chuang, A. Y., Kerr, P. D., Fest, T., Boukamp, P., and Mai, S. (2005) *Proc Natl Acad Sci USA* 102, 9613-9618
Klewes, L., Höbsch, C., Katzir, N., Rourke, D., Garini, Y., and Mai, S. (2011) *Cytometry Part A* 79A, 159-166.47.
Knecht H, Sawan B, Lichtensztejn Z, Lichtensztejn D, Mai S. *Lab Invest.* 2010; 90(4):611-619).
Blackburn E H (1991) Structure and function of telomeres. Nature 350, 569-73.
de Lange T (2002) Protection of mammalian telomeres. Oncogene 21, 532-40.
Harley C B, Futcher A B, Greider C W (1990) Telomeres shorten during ageing of human fibroblasts. Nature 345, 458-60.
Huffman K E, Levene S D, Tesmer V M, Shay J W, Wright W E. (2000) Telomere shortening is proportional to the size of the G-rich telomeric 3'-overhang. J Biol Chem 275, 19719-22.
Charames G S, Bapat B (2003) Genomic instability and cancer. Curr Mol Med 3, 589-96.

Holland A J, Cleveland D W (2009) Boveri revisited: chromosomal instability, aneuploidy and tumorigenesis. Nat Rev Mol Cell Biol 10, 478-87.

Lothe R A, Peltomaki P, Meling G I (1993) Genomic instability in colorectal cancer: relationship to clinicopathological variables and family history. Cancer Res 53, 5849-52.

Colleu-Durel S, Guitton N, Nourgalieva K, Leveque J, Danic B, Chenal C (2001) Genomic instability and breast cancer. Oncol Rep 8, 1001-5.

Chan S W, Blackburn E H (2002) New ways not to make ends meet: telomerase, DNA damage proteins and heterochromatin. Oncogene 21, 553-63.

Hayflick, L (1979) The Cell Biology of Aging. Journal of Investigative Dermatology 73, 8-14.

Sohal R S, Allen R G (1985) Relationship between metabolic rate, free radicals, differentiation and aging: a unified theory. Basic Life Sci 35, 75-104.

Yu C E, Oshima J, Fu Y H (1996) Positional cloning of the Werner's syndrome gene. Science 272, 258-62.

Shen J C, Gray M D, Oshima J, Kamath-Loeb A S, Fry M, Loeb L A (1998). Werner syndrome protein. I. DNA helicase and dna exonuclease reside on the same polypeptide. J Biol Chem 273, 34139-44.

Fry M, Loeb L A (1999). Human werner syndrome DNA helicase unwinds tetrahelical structures of the fragile X syndrome repeat sequence d(CGG)n. J Biol Chem 274, 12797-802.

Burns A, Byrne E J, Maurer K (2002) Alzheimer's disease. Lancet 360, 163-5.

Panossian L A, Porter V R, Valenzuela H F (2003) Telomere shortening in T cells correlates with Alzheimer's disease status. Neurobiol Aging 24, 77-84.

Thomas P, Hecker J, Faunt J, Fenech M (2007) Buccal micronucleus cytome biomarkers may be associated with Alzheimer's disease. Mutagenesis 22, 371-9.

Du A T, Schuff N, Amend D (2001) Magnetic resonance imaging of the entorhinal cortex and hippocampus in mild cognitive impairment and Alzheimer's disease. J Neurol Neurosurg Psychiatry 71, 441-7.

Haroutunian V, Perl D P, Purohit D P (1998) Regional distribution of neuritic plaques in the nondemented elderly and subjects with very mild Alzheimer disease. Arch Neurol 55, 1185-91.

Mattson M P (2004) Pathways towards and away from Alzheimer's disease. Nature 430, 631-9.

Kawas C H (2003) Clinical practice. Early Alzheimer's disease. N Engl J Med 349, 1056-63.

Iqbal K, Alonso A C, Gong C X (1998) Mechanisms of neurofibrillary degeneration and the formation of neurofibrillary tangles J Neural Transm Suppl 53, 169-80.

Petkova A T, Ishii Y, Balbach J J (2002) A structural model for Alzheimer's beta-amyloid fibrils based on experimental constraints from solid state NMR. Proc Natl Acad Sci USA 99, 16742-7.

Antzutkin O N, Leapman R D, Balbach J J, Tycko R (2002) Supramolecular structural constraints on Alzheimer's beta-amyloid fibrils from electron microscopy and solid-state nuclear magnetic resonance. Biochemistry 41, 15436-50.

Thomas P, NJ OC, Fenech M (2008) Telomere length in white blood cells, buccal cells and brain tissue and its variation with ageing and Alzheimer's disease. Mech Ageing Dev 129, 183-90.

Cawthon R M, Smith K R, O'Brien E, Sivatchenko A, Kerber R A (2003) Association between telomere length in blood and mortality in people aged 60 years or older. Lancet 361, 393-5.

Honig S L, Tang M X, Albert S, Costa R (2003) Stroke and the Risk of Alzheimer Disease. Archives of Neurology 60, 1707-1712.

Lukens J N, Van Deerlin V, Clark C M, Xie S X, Johnson F B (2009) Comparisons of telomere lengths in peripheral blood and cerebellum in Alzheimer's disease. Alzheimers Dement 5, 463-9.

Vermolen B J, Garini Y, Mai S (2005) Characterizing the three-dimensional organization of telomeres. Cytometry A 67, 144-50.

McKhann G, Drachman D, Folstein M, Katzman R, Price D, Stadlan E M (1984) Clinical diagnosis of Alzheimer's disease: report of the NINCDS-ADRDA Work Group under the auspices of Department of Health and Human Services Task Force on Alzheimer's Disease. Neurology 34, 939-44.

Hogan D B, Bailey P, Black S. Diagnosis and treatment of dementia: 5. (2008) Nonpharmacologic and pharmacologic therapy for mild to moderate dementia. CMAJ 176, 1019-1026.

Nasreddine Z S, Phillips N A, Bedirian V (2005) The Montreal Cognitive Assessment, MoCA: a brief screening tool for mild cognitive impairment. J Am Geriatr Soc 53, 695-9.

Folstein M F, Folstein S E, McHugh P R (1975)"Mini-mental state". A practical method for grading the cognitive state of patients for the clinician. J Psychiatr Res 12, 189-98.

Knecht H, Sawan B, Lichtensztejn D, Lemieux B, Wellinger R J, Mai S. (2009) The 3D nuclear organization of telomeres marks the transition from Hodgkin to Reed-Sternberg cells. Leukemia 23, 565-73.

Knecht H, Bruderlein S, Wegener S, Mai S (2010) 3D nuclear organization of telomeres in the Hodgkin cell lines U-HO1 and U-HO1-PTPN1: PTPN1 expression prevents the formation of very short telomeres including "t-stumps". BMC Cell Biol 11, 99-102

Schaefer L H, Schuster D, Herz H (2010) Generalized approach for accelerated maximum likelihood based image restoration applied to three-dimensional fluorescence microscopy. J Microsc 204, 99-107.

Poon S S, Martens U M, Ward R K, Lansdorp P M (1999) Telomere length measurements using digital fluorescence microscopy. Cytometry 36, 267-78.

Mai S, Garini Y (2006) The significance of telomeric aggregates in the interphase nuclei of tumor cells. J Cell Biochem 97, 904-15.

Milyaysky M, Mimran A, Senderovich S (2001) Activation of p53 protein by telomeric (TTAGGG)n repeats. Nucleic Acids Res 29, 5207-15.

Farazi P A, Glickman J, Horner J, Depinho R A (2006) Cooperative interactions of p53 mutation, telomere dysfunction, and chronic liver damage in hepatocellular carcinoma progression. Cancer Res 66, 4766-73.

Myung N H, Zhu X, Kruman, I I (2008) Evidence of DNA damage in Alzheimer disease: phosphorylation of histone H2AX in astrocytes. Age (Dordr) 30, 209-15.

Coppede F, Migliore L (2009) DNA damage and repair in Alzheimer's disease. Curr Alzheimer Res 6, 36-47.

Mirzoeva O K, Petrini J H (2001) DNA damage-dependent nuclear dynamics of the Mre11 complex. Mol Cell Biol 21, 281-8.

Delmas S, Shunburne L, Ngo H P, Allers T (2009) Mre11-Rad50 promotes rapid repair of DNA damage in the polyploid archaeon Haloferax volcanii by restraining homologous recombination. PLoS Genet 5, e1000552.

Jacobson S J, Laurenson P M, Pillus L (2004) Functional analyses of chromatin modifications in yeast. Methods Enzymol 377, 3-55.

Davydov V, Hansen L A, Shackelford D A (2003) Is DNA repair compromised in Alzheimer's disease? Neurobiol Aging 24, 953-68.

Davydov V, Hansen L A, Shackelford D A (2003) Is DNA repair compromised in Alzheimer's disease? Neurobiol Aging 24, 953-68.

Shackelford D A (2006) DNA end joining activity is reduced in Alzheimer's disease. Neurobiol Aging 27, 596-605.

Dhillon V S, Thomas P, Fenech M (2004) Comparison of DNA damage and repair following radiation challenge in buccal cells and lymphocytes using single-cell gel electrophoresis. Int J Radiat Biol 80, 517-28.

Carlin V, Matsumoto M A, Saraiva P P, Artioli A, Oshima C T, Ribeiro D A (2011) Cytogenetic damage induced by mouthrinses formulations in vivo and in vitro. Clin Oral Investig.

Thomas P, Fenech M (2008) Chromosome 17 and 21 aneuploidy in buccal cells is increased with ageing and in Alzheimer's disease. Mutagenesis 23, 57-65.

Lechel A, Satyanarayana A, Ju Z (2005) The cellular level of telomere dysfunction determines induction of senescence or apoptosis in vivo. EMBO. Rep 6, 275-81.

Herbig U, Sedivy J M (2006) Regulation of growth arrest in senescence: telomere damage is not the end of the story. Mech Ageing Dev 127, 16-24.

de Lange T. (2005) Shelterin: the protein complex that shapes and safeguards human telomeres. Genes Dev 19, 2100-10.

van Steensel B, Smogorzewska A, de Lange T (1998) TRF2 protects human telomeres from end-to-end fusions. Cell 92, 401-13.

Smogorzewska A, de Lange T (2002) Different telomere damage signaling pathways in human and mouse cells. EMBO J 21, 4338-48.

Umen J G (2005) The elusive sizer. Curr Oppinion in Cell Biology 17, 435-441

Echave P, Conlon A C, Lioyd C (2007) Cell size regulation in mammalian cells. Cell Cycle. 6, 218-224.

Broers J L, Ramaekers F C, Bonne G, Yaou R B, Hutchison C J (2006) Nuclear lamins: laminopathies and their role in premature ageing. Physiol Rev 86, 967-1008.

Taddei A, Hediger F, Neumann F R, Gasser S M (2004) The function of nuclear architecture: a genetic approach. Annu. Rev Genet 38, 305-45.

Dechat T, Pfleghaar K, Sengupta K, Shimi T, Shumaker D K, Solimando L, Goldman R D (2008)
Nuclear lamins: major factors in the structural organization and function of the nucleus and chromatin. Genes Dev 22, 832-53.

Mounkes L C, Stewart C L (2004). Aging and nuclear organization: lamins and progeria. Curr Opin Cell Biol 16, 322-327.

Huang S, Risques R A, Martin G M, Rabinovitch P S, Oshima J (2008) Accelerated telomere shortening and replicative senescence in human fibroblasts overexpressing mutant and wild-type lamin A. Exp Cell Res 314, 82-91.

Prokocimer M, Davidovich M, Nissim-Rafinia M, Wiesel-Motiuk N, Bar D, Barkan R, Meshorer E, Gruenbaum Y (2009) Nuclear lamins: key regulators of nuclear structure and activities. J Cell Mol Med 13, 1059-1085.

Raz V, Vermolen B J, Garini Y, Onderwater J J, Mommaas-Kienhuis M A, Koster A J, Young I T, Tanke H, Dirks R W (2008) The nuclear lamina promotes telomere aggregation and centromere peripheral localization during senescence of human mesenchymal stem cells. J Cell Sci 121, 4018-4028.

Gonzalez-Suarez I, Redwood A B, Perkins S M, Vermolen B, Lichtensztejin D, Grotsky D A, Morgado-Palcin L, Gapud E J, Sleckman B P, Sulivan T, Sage J, Steward C L, Mai S, Gonzalo S (2009) Novel roles for A type lamins in telomere biology and DNA damage response pathway EMBO J 28, 2414-27.

Mai S, Garini Y (2005) Oncogenic remodeling of the three-dimensional organization of the interphase nucleus: c-Myc induces telomeric aggregates whose formation precedes chromosomal rearrangements. Cell Cycle 4, 1327-31.

Gadji M, Fortin D, Tsanacils A M (2010) Three-dimentional Nuclear Telomere architecture is associated with differential time to progression and overall survival in glioblastoma patients. Neoplasia 12, 183-191.

Louis S F, Vermolen B J, Garini Y, Mai S (2005) c-Myc induces chromosomal rearrangements through telomere and chromosome remodeling in the interphase nucleus. Proc Natl Acad Sci USA 102, 9613-8.

Guffei A, Sarkar R, Klewes L, Righolt C, Knecht H, Mai S (2010) Dynamic chromosomal rearrangements in Hodg'in's lymphoma are due to ongoing three-dimensional nuclear remodeling and breakage-bridge-fusion cycles. Haematologica 95, 2038-46.

Watson J D (1972) Origin of concatemic T7 DNA. Nat New Biol 239, 197-201.

Olovnikov A M (1972) The immune response and the process of marginotomy in lymphoid cells. Vestn Akad Nauk SSSR 27, 85-87.

Kruk P A, Rampino N J, Bohr V A (1995) DNA damage and repair in telomeres: relation to aging. Proc Natl Acad Sci USA 92, 258-262.

Wynford-Thomas D, Kipling D (1997) The end replication problem. Nature 389, 551.

Allsopp R C, Vaziri H, Patterson C, Goldstein S, Younglai E V, Futcher A B, Greider C W, Harley C B (1992) Telomere length predicts replicative capacity of human fibroblasts. Proc Natl Acad Sci USA 89, 10114-10118.

Kipling D, Wynford-Thomas D, Jones C J, Akbar A, Aspinall R, Bacchetti S, Blasco M A, Broccoli D, DePinho R A, Edwards D R, Effros R B, Harley C B, Lansdorp P M, Linskens M H, Prowse K R, Newbold R F, Olovnikov A M, Parkinson E K, Pawelec G, Ponten J, Shall S, Zijlmans M, Faragher R G (1999) Telomere-dependant senescence. Nat Biotechnol 17, 313-314.

Greider C W, Blackburn E H (1985) Identification of a specific telomere terminal transferase activity in Tetrahymena extracts. Cell 43, 405-413.

Wojtyla A, Gladych M, Rubis B (2011) Human telomerase activity regulation. Mol Biol Rep 38, 3339-3349.

Muntoni A, Rendel R R (2005) The first molecular details of ALT in human tumor cells. Hum Mol Genet 14, R191-R196.

Vaziri H, Schachter F, Uchida I, Wei L, Zhu X, Effros R, Cohen D, Harley C B (1993) Loss of telomeric DNA during aging or normal and trisomy 21 human lymphocytes. Am J Hum Genet 52, 661-667.

Mai S (2010) Initiation of telomere-mediated chromosomal rearrangement in cancer. J Cell Biochem 109, 1095-1102.

Meeker A K, Hicks J L, Iacobuzio-Donahue C A, Montgomery E A, Westra W H, Chan T Y, Ronnett B M, De Marzo A M (2004) Telomere length abnormalities occur early in the initiation of epithelial carcinogenesis. Clin Cancer Res 10, 3317-3326.

Rampazzo E, Bertorelle R, Serra L, Terrin L, Candiotto C, Pucciarelli S, Del Bianco P, Nitti D, De Rossi A (2010) Relationship between telomere shortening, genomic instability, and site of tumor origin in colorectal cancers. Br J Cancer 102, 1300-1305.

Epel E S, Merkin S S, Cawthon R, Blackburn E H, Adler N E, Pletcher M J, Seeman T E (2008) The rate of leukocyte telomere shortening predicts mortality from cardiovascular disease in elderly men. Aging (Albany N.Y.) 1, 81-88.

Balasubramanyam M, Adaikalakoteswari A, Monickaraj S F, Mohan V (2007) Telomere shortening and metabolic/vascular diseases. The Indian J Med Res 125, 441-450.

Vulliamy T, Marrone A, Szydlo R, Walne A, Mason P J, Dokal I (2004) Disease anticipation is associated with progressive telomere shortening in families with dyskeratosis congenital due to mutations in TERC. Nat Genet 36, 447-449.

Bessler M, Du H Y, Gu B, Mason P J (2007) Dysfunctional telomeres and dyskeratosis congenita. Haematologica 92, 1009-1012.

Samani N J, Boultby R, Butler R, Thompson J R, Goodall A H (2001) Telomere shortening in atherosclerosis. Lancet 11, 472-473.

Jenkins E C, Velinov M T, Ye L, Gu H, Li S, Jenkins E C Jr, Brooks S S, Pang D, Devenny D A, Zigman W B, Schupf N, Silverman W P (2006) Telomere shortening in T lymphocytes of older individuals with Down syndrome and dementia. Neurobiol Aging 27, 941-945.

Kume K, Kikukawa M, Hanyu H, Takata Y, Umahara T, Sakurai H, Kanetaka H, Ohyashiki K, Ohyashiki J H, Iwamoto T (2012) Telomere length shortening in patients with dementia with Lewy bodies. Eur J Neurol 19, 905-910.

Jenkins E C, Ye L, Gu H, Ni S A, Duncan C J, Velinov M, Pang D, Krinsky-McHale S J, Zigman W B, Schupf N, Silverman W P (2008) Increased "absence" of telomeres may indicate Alzheimer's disease/dementia status in older individuals with Down syndrome. Neurosci Lett 440, 340-343.

Maeda T, Guan J Z, Koyanagi M, Higuchi Y, Makino N (2012) Aging-associated alteration of telomere length and subtelomeric status in female patients with Parkinson's disease. J Neurogenet 26, 245-251.

Alzheimer's Association (2012) 2012 Alzheimer's disease facts and figures. Alzheimer's and Dementia: The Journal of the Alzheimer's Association 8, 131-168.

Alzheimer Society of Canada, http://www.alzheimer.ca/en/About-dementia/Alzheimer-s-disease/What-is-Alzheimer-s-disease, Last updated Mar. 1, 2013, Accessed on Mar. 6, 2013.

Frank E M (1994) Effect of Alzheimer's disease on communication function. J S C Med Assoc 90, 417-423.

Forstl H, Kruz A (1999) Clinical features of Alzheimer's disease. European Archives of Psychiatry and Clinical Neuroscience 249, 288-290.

Taler V, Phillips N A (2008) Language performance in Alzheimer's disease and mild cognitive impairment: a comparative review. J Clin Exp Neuropsychol 30, 501-556.

Brookmeyer R, Johnson E, Ziegler-Graham K, Arrighi H M (2007) Forecasting the global burden of Alzheimer's disease. Alzheimers Dement 3, 186-191.

World population prospects: the 2010 revision highlights, http://esa.un.org/wpp/Documentation/pdf/WPP2010_Highlights.pdf, Accessed on Mar. 8, 2013.

Mölsä P K, Marttila R J, Rinne U K (1986) Survival and cause of death in Alzheimer's disease and multi-infarct dementia. Acta Neurol Scand 74, 103-107.

Mölsä P K, Marttila R J, Rinne U K (1995) Long-term survival and predictors of mortality in Alzheimer's disease and multi-infarct dementia. Acta Neurol Scand 91, 159-164.

Migliore L, Testa A, Scarpato R, Pavese N, Petrozzi L, Bonuccelli U (1997) Spontaneous and induced aneuploidy in peripheral blood lymphocytes of patients with Alzheimer's disease. Hum Genet 101, 299-305.

Migliore L, Botto N, Scarpato R, Petrozzi L, Cipriani G, Bonuccelli U (1999) Preferential occurrence of chromosome 21 malsegregation in peripheral blood lymphocytes of Alzheimer's disease patients. Cytogenet Cell Genet 87, 41-46.

Geller L N, Potter H (1999) Chromosome missegregation and trisomy 21 mosaicism in Alzheimer's disease. Neurobiol Dis 6, 167-179.

Juan J Z, Guan W P, Maeda T, Makino N (2012) Effect of vitamin E administration on the elevated oxygen stress and the telomeric and subtelomeric status in Alzheimer's disease. Gerontology 58, 62-69.

Nazarenko S A, Timoshevsky V A, Sukhanova N N (1999) High frequency of tissue-specific mosaicism in Turner Syndrome patients. Clin Genet 56, 59-65.

Dubois B, Feldman H H, Jacova C, Dekosky S T, Barberger-Gateau P, Cummings J, Delacourte A, Galasko D, Gauthier S, Jicha G, Meguro K, O'Brien J, Pasquier F, Robert P, Rossor M, Salloway S, Stern Y, Visser P J, Scheltens P (2007) Research criteria for the diagnosis of Alzheimer's disease: revising the NINCDS-ADRDA criteria. Lancet Neurol 6, 734-746.

Nasreddine Z S, Phillips N A, Bedirian V, Charbonneau S, Whitehead V, Collin I, Cummings J L, Chertkow H (1995) The Montreal Cognitive Assessment, MoCA: a brief screening tool for mild cognitive impairment. J Am Geriatr Soc 53, 695-699.

McDowell I, Kristjansson B, Hill G B, Hebert R (1997) Community screening for dementia: the Mini Mental State Exam (MMSE) and Modified Mini-Mental State Exam (3M S) compared. J Clin Epidemiol 50, 377-383.

Herrmann N, Gauthier S (2008) Diagnosis and treatment of dementia: 6. Management of severe Alzheimer disease. CMAJ 179, 1279-1287.

Gauthier S, Patterson C, Chertkow H, Gordon M, Herrmann N, Rockwood K, Rosa-Neto P, Soucy J P (2012) 4th Canadian consensus conference on the diagnosis and treatment of dementia. Can J Neurol Sci 39, S1-S8.

Cremer M, Grasser F, Lanctot C, Muller S, Neusser M, Zinner R, Solovei I, Cremer T (2008) Multicolor 3D fluorescence in situ hybridization for imaging interphase chromosomes. Methods Mol Biol 463, 205-239.

Gustafsson M. G. L (2000) Surpassing the lateral resolution limit by a factor of two using structured illumination microscopy. J. Microsc. 198, 82-87.

Nagele R G, Velasco A Q, Anderson W J, McMahon D J, Thomson Z, Fazekas J, Wind K, Lee H (2001) Telomere associations in interphase nuclei: possible role in maintenance of interphase chromosome topology. Journal of Cell Science 114, 377-388.

Weierich C, Brero A, Stein S, von Hasse J, Cremer C, Cremer T, Solovei I (2003) Three-dimensional arrangements of centromeres and telomeres in nuclei of human and murine lymphocytes. Chromosome Res 11, 485-502.

De Vos W H, Hoebe R A, Joss G H, Haffmans W, Baatout S, Van Oostveldt P, Manders E M (2009) Controlled light exposure microscopy reveals dynamic telomere microterritories throughout the cell cycle. Cytometry A 75, 428-439.

Knecht H, Righolt C, Mai S (2013) Genomic Instability: The Driving Force behind Refractory/Relapsing Hodgkin's Lymphoma. Cancers 5, 7140725.

Duda R. O, Hart P. E (1973) Pattern Classification and Scene Analysis. Wiley-Interscience 1st edition, New York, N.Y., USA.

Adebayo Awe J, Xu M C, Wechsler J, Benali-Furet N, Cayre Y E, Saranchuk J, Drachenberg D, Mai S (2013) Three-dimensional telomeric analysis of isolated circulating tumor cells (CTCs) defines CTC subpopulations. Translational Oncology 6, 51-65.

Gadji M, Adebayo Awe J, Rodrigues P, Kumar R, Houston D S, Klewes L, Dieye T N, Rego E M, Passetto R F, de Oliveira F M, Mai S (2012) Profiling three-dimensional nuclear telomeric architecture of myelodysplastic syndromes and acute myeloid leukemia defines patient subgroups. Clinical Cancer Research 18, 3293-3304.

Sukenik-Halevy R, Fejgin M, Kidron D, Goldberg-Bittman L, Sharony R, Biron-Shental T, Kitay-Cohen Y, Amiel A (2009) Telomere aggregate formation in placenta specimens of pregnancies complicated with pre-eclampsia. Cancer Genet Cytogenet 195, 27-30.

Biron-Shental T, Sukenik-Halevy R, Sharon Y, Goldberg-Bittman L, Kidron D, Fejgin M D, Amiel A (2010) Short telomeres may play a role in placental dysfunction in preeclapsia and intrauterine growth restriction. Am J Obstet Gynecol 202, 381.

Hadi E, Sharony R, Goldberg-Bittman L, Biron-Shental T, Fejgin M, Amiel A (2009) Telomere aggregates in trisomy 21 amniocytes. Cancer Genet Cytogenet 195, 23-26.

Righolt C H, van't Hoff M L, Vermolen B J, Young I T, Raz V (2011) Robust nuclear lamina-based cell classification of aging and senescent cells. Aging (Albany N.Y.) 3, 1192-1201.

Sfeir A, de Lange T (2012) Removal of Shelterin Reveals the Telomere End-Protection Problem. Science 336, 593-597.

Jacobs E G, Kroenke C, Lin J, Epel E S, Kenna H A, Blackburn E H, Rasgon N L (2013) Accelerated cell aging in female APOE-e4 carriers: implications for hormone therapy use. PLoS One 8, e54713.

Epel E S, Blackburn E H, Lin J, Dhabhar F S, Adler N E, Morrow J D, Cawthon R M (2004) Accelerated telomere shortening in response to life stress. Proc Natl Acad Sci USA 101, 17312-17315.

Riudavets M, Iacono D, Resnick S M, O'Brien R, Zonderman A B, Martin L J, Rudow G, Pletnikova O, Troncoso J C (2007) Resistance to Alzheimer's pathology is associated with nuclear hypertrophy in neurons. Neurobiology of Aging 10, 1484-1492.

Klewes 2011 Novel automated three-dimensional genome scanning based on the nuclear architecture of telomeres. Cytometry 79:159-66.

Mai S, Wiener F. Murine FISH. In: Beatty M, Mai S, Squire J, editors. FISH: A Practical Approach. Oxford, U K: Oxford University Press; 2002. pp 55-67

The invention claimed is:

1. A method for evaluating and/or diagnosing a human subject as having Alzheimer's disease (AD), comprising:
   a) obtaining a test buccal cell sample from the subject having AD, the obtaining the test buccal cell sample comprising swabbing the inside of the cheek of the subject to collect buccal cells and smearing the buccal cells on a microscope slide;
   b) assaying the test buccal cell sample using three-dimensional quantitative fluorescent in situ hybridization (3D q-FISH) to determine a test buccal cell sample telomere organization signature, the assaying comprising:
      i. nuclear staining the test buccal cell sample by hybridizing the test buccal cell sample with a labelled probe,
      ii. mounting the test buccal cell sample using an antifade mounting medium,
      iii. 3D imaging the test buccal cell sample, and
      iv. measuring on the 3D image values for telomere parameters, the telomere parameters comprising average number of telomere aggregates, average telomere length and average telomere number to obtain the test buccal cell sample telomere organization signature;
   c) comparing the test buccal cell sample telomere organization signature to one or more predetermined reference telomere organization signatures, each reference telomere organization signature comprising a control and/or values for the telomere parameters; and
   d) evaluating and/or diagnosing the subject as having AD or likely to develop AD, when i. an increase in average number of telomere aggregates, ii. an increase in average telomere number and iii. a decrease in average telomere length in the test buccal cell sample telomere organization signature compared to a reference telomere organization signatures is detected.

2. The method of claim 1, wherein the subject is diagnosed as having AD when the average number of telomere aggregates is at least 3.5 per cell, 3.6 per cell, 3.7 per cell, 3.8 per cell, 3.9 per cell, 4.0 per cell, 4.1 per cell, 4.2 per cell, 4.3 per cell, 4.4 per cell or 4.5 per cell, optionally wherein the AD severity is determined as moderate when the average number of telomere aggregates is at least 3.7 per cell, 3.8 per cell or 3.9 per cell, the AD severity is determined as severe when the average number of telomere aggregates is at least 4.0 per cell, 4.1 per cell, 4.2 per cell, 4.3 per cell, 4.4 per cell or 4.5 per cell.

3. The method of claim 1, wherein an average telomere number greater than 65, greater than 70, greater than 80, or greater than 85 per cell is indicative of AD or an increased likelihood of developing AD, optionally wherein an average telomere number greater than about 65, about 70 or about 75 per cell is indicative of moderate AD and an average telomere number greater than about 80 or about 85 per cell is indicative of severe AD.

4. The method of claim 1, wherein the q-FISH is FISH for individual genes, chromosomes, chromosomal regions or centromeres, immunocytochemistry, immunohistochemistry, histology and/or histochemistry.

5. The method of claim 1, wherein the average telomere length is measured in base pairs, optionally wherein a decrease in the proportion of long telomeres and an increase in the proportion of short telomeres in the test buccal cell sample telomere organization signature compared to the reference telomere organization signature is indicative of AD or an increased likelihood of developing AD.

6. The method of claim 5, wherein a decrease in average telomere length of at least 200, at least 270, at least 300, at least 400, at least 500, at least 600, at least 700, at least 800, at least 900, at least 1000, at least 1100, at least 1200, at least 1300, at least 1400, at least 1480, at least 1500, at least 1600, at least 1700, at least 1800, at least 1900, at least 2000, at least 2100, at least 2200, at least 2300, at least 2340, at least 2400 or at least 2500 base pairs is indicative of AD or an increased likelihood of developing AD, optionally wherein a decrease in average telomere length between about 200 and about 1000 base pairs is indicative of mild AD, a decrease in average telomere length between about 1001 and about 2000 is indicative of moderate AD and a decrease in average telomere length of greater than about 2000 is indicative of severe AD.

7. The method of claim 1, wherein the telomere organization signature is determined on interphase telomeres.

8. A method for assessing a putative Alzheimer's disease (AD) treatment and/or monitoring a human subject having AD receiving such treatment, comprising:
   a) obtaining a first test buccal cell sample from the subject having AD, the obtaining the first test buccal cell sample comprising swabbing the inside of the cheek of the subject to collect buccal cells and smearing the buccal cells on a microscope slide;
   b) administering to the subject the treatment;
   c) obtaining a subsequent test buccal cell sample from the subject having AD, the obtaining the subsequent test buccal cell sample comprising swabbing the inside of the cheek of the subject to collect buccal cells and smearing the buccal cells on a microscope slide;
   d) assaying the first and subsequent test buccal cell samples using three-dimensional quantitative fluorescent in situ hybridization (3D q-FISH) to determine a first test buccal cell sample telomere organization signature and a subsequent test buccal cell sample telomere organization signature, the assaying comprising:
      i. nuclear staining the test buccal cell samples by hybridizing each test buccal cell sample with a labelled probe,
      ii. mounting the test buccal cell samples using an antifade mounting medium,
      iii. 3D imaging the test buccal cell samples, and
      iv. measuring on the 3D images values for telomere parameters, the telomere parameters comprising average number of telomere aggregates, average telomere length and average telomere number to obtain the first test buccal cell sample telomere organization signature and the subsequent test buccal cell sample telomere organization signature;
   e) comparing the first test buccal cell sample telomere organization signature to the subsequent test buccal cell sample telomere organization signature, and
   f) identifying the treatment as efficacious or not efficacious, and/or the subject as progressing, stable or improving according to the differences or similarities between the first test buccal cell sample telomere organization signature and the subsequent test buccal cell sample telomere organization signature.

9. The method of claim 8, wherein an increase in average telomere aggregates, an increase in average telomere number, optionally an increase in average telomere number to at least 65 per cell, and a decrease in average telomere length in the subsequent test buccal cell sample telomere organization signature compared to the first test buccal cell sample telomere organization signature is indicative the subject has worsening AD and/or is not responding to the treatment.

10. The method of claim 1, wherein the predetermined reference telomere organization signature parameter values are determined from a population of subjects that are known to be AD free or to have mild AD, moderate AD or severe AD.

11. The method of claim 1 wherein the control is a threshold value associated with a population of subjects that are AD free.

12. A method of identifying if a test buccal cell sample is a sample derived from a human subject having Alzheimer's disease (AD), comprising:
   a) obtaining a test buccal cell sample from the subject having AD, the obtaining the test buccal cell sample comprising swabbing the inside of the cheek of the subject to collect buccal cells and smearing the buccal cells on a microscope slide;
   b) assaying the test buccal cell sample using three-dimensional quantitative fluorescent in situ hybridization (3D q-FISH) to determine a test buccal cell sample telomere organization signature, the assaying comprising:
      i. nuclear staining the test buccal cell sample by hybridizing the test buccal cell sample with a labelled probe,
      ii. mounting the test buccal cell sample using an antifade mounting medium,
      iii. 3D imaging the test buccal cell sample, and
      iv. measuring on the 3D image values for telomere parameters, the telomere parameters comprising average number of telomere aggregates, average telomere length and average telomere number to obtain the test buccal cell sample telomere organization signature; and
   c) identifying the test buccal cell sample as a sample derived from a human subject having AD when the test buccal cell sample comprises buccal cells with an average number of telomere aggregates of at least 3.5 per cell, an average telomere number of at least 65 per cell and an average telomere length of less than 7.4 kB.

13. The method of claim 6, wherein the 3D q-FISH is performed using a PNA telomere probe and wherein the 3D imaging comprises acquiring an image dataset of different planes of 3D q-FISH fluorescent signals and reconstructing a 3D image of the telomeres using deconvolution of the images performed with a constrained iterative algorithm.

* * * * *

UNITED STATES PATENT AND TRADEMARK OFFICE
CERTIFICATE OF CORRECTION

PATENT NO. : 9,758,830 B2  
APPLICATION NO. : 14/491996  
DATED : September 12, 2017  
INVENTOR(S) : Sabine Mai and Angeles Garcia Page 1 of 1

It is certified that error appears in the above-identified patent and that said Letters Patent is hereby corrected as shown below:

In the Claims

Column 46, Line 5 in Claim 1; Column 47, Line 29 in Claim 8; and Column 48, Line 26 in Claim 12:
-in situ- should be -*in situ*-.

Column 46, Line 40, in Claim 2:
Insert --and-- after the -,-.

Column 46, Lines 53-55, in Claim 4:
Delete "or centromeres, immunocytochemistry, immunohistochemistry, histology and/or histochemistry" and insert --or-- before -chromosomal regions-.

Signed and Sealed this
Twenty-fourth Day of April, 2018

Andrei Iancu
*Director of the United States Patent and Trademark Office*